(12) United States Patent
Kamata et al.

(10) Patent No.: US 10,925,685 B2
(45) Date of Patent: Feb. 23, 2021

(54) MEDICAL OBSERVATION DEVICE, SURGICAL OBSERVATION DEVICE, AND MEDICAL OBSERVATION SYSTEM

(71) Applicant: Sony Olympus Medical Solutions Inc., Tokyo (JP)

(72) Inventors: Yoshiyuki Kamata, Tokyo (JP); Motoaki Kobayashi, Tokyo (JP); Shigeru Tamura, Tokyo (JP); Kenji Hirose, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 15/558,664

(22) PCT Filed: Mar. 24, 2016

(86) PCT No.: PCT/JP2016/059431
§ 371 (c)(1),
(2) Date: Sep. 15, 2017

(87) PCT Pub. No.: WO2016/152987
PCT Pub. Date: Sep. 29, 2016

(65) Prior Publication Data
US 2018/0110581 A1 Apr. 26, 2018

(30) Foreign Application Priority Data

Mar. 25, 2015 (JP) .............................. JP2015-062155
Jan. 19, 2016 (JP) .............................. JP2016-007811

(51) Int. Cl.
*A61B 90/25* (2016.01)
*G02B 7/00* (2021.01)
(Continued)

(52) U.S. Cl.
CPC ............ *A61B 90/25* (2016.02); *A61B 90/361* (2016.02); *G02B 7/001* (2013.01); *G02B 21/362* (2013.01);
(Continued)

(58) Field of Classification Search
CPC ......... A61B 90/50; A61B 90/20; A61B 90/25; A61B 34/30; A61B 90/361;
(Continued)

(56) References Cited

U.S. PATENT DOCUMENTS 2,592,842 A * 4/1952 Alderson .................. A61F 2/54
623/58
3,891,301 A * 6/1975 Heller ..................... F16M 11/08
359/384
(Continued)

FOREIGN PATENT DOCUMENTS

EP 0153884 A1 * 9/1985 ............... B23Q 1/54
EP 1 582 167 A2 10/2005
(Continued)

OTHER PUBLICATIONS

International Search Report dated May 24, 2016 in PCT/JP2016/059431 filed Mar. 24, 2016.
(Continued)

*Primary Examiner* — David E Harvey
(74) *Attorney, Agent, or Firm* — Xsensus LLP

(57) ABSTRACT

Provided is a medical observation device including an imaging unit configured to capture an image of an object to be observed, and output a video signal, and a support unit configured with a plurality of arm units rotatably connected to each other via joint units, and configured to support the imaging unit. An actuator that applies driving force with respect to rotation about a rotational axis of at least one joint unit that defines an attitude of the imaging unit, among a
(Continued)

plurality of the joint units that form the support unit, is provided. The at least one joint unit and the actuator are arranged separated from each other, and are connected together via a power transmission mechanism that transmits rotary movement between two rotational axes that are substantially orthogonal to each other.

22 Claims, 12 Drawing Sheets

(51) Int. Cl.
    *A61B 90/00* (2016.01)
    *G02B 21/36* (2006.01)
    *G02B 21/00* (2006.01)
    *A61B 34/20* (2016.01)
    *A61B 90/50* (2016.01)

(52) U.S. Cl.
    CPC . *A61B 2034/2059* (2016.02); *A61B 2090/371* (2016.02); *A61B 2090/504* (2016.02); *A61B 2090/506* (2016.02); *G02B 21/0012* (2013.01)

(58) Field of Classification Search
    CPC .......... A61B 1/00149; A61B 34/71; A61B 2017/00477; B25J 9/0084; B25J 9/06; B25J 9/08; B25J 9/009; B25J 17/02; B25J 17/0283; B25J 9/126; B25J 15/022; Y10T 74/20317; Y10T 74/20305; Y10T 74/20335; Y10T 74/20329; Y10S 901/23–26
    See application file for complete search history.

(56) References Cited

U.S. PATENT DOCUMENTS

| | | | | |
|---|---|---|---|---|
| 4,188,166 | A * | 2/1980 | Moreau | B25J 9/06 414/4 |
| 4,344,595 | A * | 8/1982 | Heller | F16M 11/08 248/542 |
| 4,515,333 | A * | 5/1985 | Pugh | F16C 11/106 248/123.11 |
| 4,561,816 | A * | 12/1985 | Dingess | B23K 9/0288 165/11.1 |
| 4,662,814 | A * | 5/1987 | Suzuki | B25J 9/06 414/730 |
| 4,780,047 | A * | 10/1988 | Holt | B25J 3/04 414/730 |
| 4,922,782 | A * | 5/1990 | Kawai | B25J 9/0084 29/402.08 |
| 4,964,503 | A * | 10/1990 | Nishiyama | B25J 9/104 192/12 D |
| 4,973,215 | A * | 11/1990 | Karlen | B25J 9/04 414/729 |
| 5,054,725 | A * | 10/1991 | Bucefari | F16M 11/126 248/123.11 |
| 5,178,032 | A * | 1/1993 | Zona | B25J 17/025 74/479.01 |
| 5,184,601 | A * | 2/1993 | Putman | B25J 9/042 312/209 |
| 5,230,623 | A * | 7/1993 | Guthrie | G06F 3/0346 33/513 |
| 5,343,391 | A * | 8/1994 | Mushabac | A61C 13/0004 433/76 |
| 5,553,198 | A * | 9/1996 | Wang | A61B 34/70 606/19 |
| 5,580,209 | A * | 12/1996 | Ogawa | B25J 9/1065 414/729 |
| 5,657,429 | A * | 8/1997 | Wang | A61B 34/70 600/118 |
| 5,667,186 | A * | 9/1997 | Luber | F16M 11/08 248/550 |
| 5,855,583 | A * | 1/1999 | Wang | A61B 17/11 318/568.11 |
| 6,105,909 | A * | 8/2000 | Wirth | A61B 90/25 248/123.2 |
| 6,309,403 | B1 * | 10/2001 | Minor | A61B 17/29 606/205 |
| 6,361,570 | B1 * | 3/2002 | Gow | A61F 2/54 623/62 |
| 6,470,236 | B2 * | 10/2002 | Ohtsuki | B25J 9/1689 345/157 |
| 6,661,571 | B1 * | 12/2003 | Shioda | A61B 1/04 359/368 |
| 6,978,193 | B2 * | 12/2005 | Kamon | B25J 9/1653 318/568.1 |
| 7,109,678 | B2 * | 9/2006 | Kraus | F16M 11/105 248/280.11 |
| 7,189,246 | B2 * | 3/2007 | Otsuka | A61B 90/50 600/102 |
| 7,492,116 | B2 * | 2/2009 | Oleynikov | A61B 1/041 318/568.12 |
| 8,006,850 | B2 * | 8/2011 | Rotheisler | B66C 23/14 212/196 |
| 8,677,854 | B2 * | 3/2014 | Lundberg | B25J 9/04 74/490.01 |
| 8,834,489 | B2 * | 9/2014 | Cooper | A61B 90/10 606/130 |
| 9,291,793 | B2 * | 3/2016 | Cooper | B25J 19/0016 |
| 10,114,208 | B2 * | 10/2018 | Kamata | G02B 21/24 |
| 2001/0030683 | A1 * | 10/2001 | Howell | E04B 9/006 348/61 |
| 2003/0010148 | A1 * | 1/2003 | Okamoto | B25J 17/0291 74/490.05 |
| 2003/0069471 | A1 * | 4/2003 | Nakanishi | A61B 1/0005 600/101 |
| 2003/0208189 | A1 * | 11/2003 | Payman | A61F 9/008 606/5 |
| 2003/0218720 | A1 * | 11/2003 | Morita | A61B 1/00048 351/222 |
| 2004/0024311 | A1 * | 2/2004 | Quaid, III | A61B 17/3403 600/428 |
| 2004/0111183 | A1 * | 6/2004 | Sutherland | A61B 90/25 700/245 |
| 2004/0138524 | A1 * | 7/2004 | Ueda | A61B 90/50 600/102 |
| 2004/0190131 | A1 * | 9/2004 | Brenner | F16M 11/10 359/384 |
| 2004/0246469 | A1 * | 12/2004 | Hirose | A61B 1/00048 356/139.03 |
| 2005/0029978 | A1 * | 2/2005 | Oleynikov | A61B 1/041 318/568.12 |
| 2005/0228257 | A1 | 10/2005 | Ishikawa et al. | |
| 2006/0252004 | A1 * | 11/2006 | Donahoo | A61C 19/00 433/29 |
| 2007/0095582 | A1 * | 5/2007 | Stuijt | A61G 5/10 180/65.1 |
| 2008/0267472 | A1 * | 10/2008 | Demos | A61B 1/00009 382/128 |
| 2009/0173846 | A1 * | 7/2009 | Katz | A61B 90/50 248/124.1 |
| 2009/0283647 | A1 * | 11/2009 | Yasunaga | A61B 90/50 248/123.2 |
| 2010/0245549 | A1 * | 9/2010 | Allen | A61B 1/00183 348/65 |
| 2012/0228435 | A1 * | 9/2012 | Vance | B64G 4/00 244/172.4 |
| 2013/0174680 | A1 * | 7/2013 | Mihara | F16H 19/08 74/98 |
| 2013/0345717 | A1 * | 12/2013 | Markvicka | A61B 34/30 606/130 |
| 2014/0157937 | A1 * | 6/2014 | Doi | F16M 11/2021 74/490.01 |
| 2015/0085095 | A1 * | 3/2015 | Tesar | A61B 1/005 348/77 |
| 2015/0250547 | A1 * | 9/2015 | Fukushima | G05B 15/02 606/130 |

(56) References Cited

U.S. PATENT DOCUMENTS

| | | | | |
|---|---|---|---|---|
| 2015/0327765 | A1* | 11/2015 | Crane | A61B 5/0059 |
| | | | | 348/77 |
| 2016/0072366 | A1* | 3/2016 | Omata | H02K 5/10 |
| | | | | 310/51 |
| 2016/0113728 | A1* | 4/2016 | Piron | A61B 17/3421 |
| | | | | 606/130 |
| 2016/0270867 | A1* | 9/2016 | Scholan | B25J 19/04 |
| 2016/0303745 | A1* | 10/2016 | Rockrohr | A61B 34/71 |
| 2017/0014197 | A1* | 1/2017 | McCrea | B25J 15/0226 |
| 2017/0251990 | A1* | 9/2017 | Kheradpir | B25J 5/007 |
| 2018/0264640 | A1* | 9/2018 | Holloway | B25J 1/08 |
| 2018/0289445 | A1* | 10/2018 | Krinninger | B25J 13/084 |

FOREIGN PATENT DOCUMENTS

| | | | | | |
|---|---|---|---|---|---|
| FR | 3006418 | A1 | * | 12/2014 | ............ F16M 11/08 |
| GB | 2540756 | A | * | 2/2017 | ......... B25J 17/0275 |
| JP | 60-080591 | A | | 5/1985 | |
| JP | 5-228878 | A | | 9/1993 | |
| JP | 05228878 | A | * | 9/1993 | |
| JP | 6-148528 | A | | 5/1994 | |
| JP | 07195291 | A | * | 8/1995 | |
| JP | 2004-267774 | A | | 9/2004 | |
| JP | 2005-524442 | A | | 8/2005 | |
| JP | 2005-292320 | A | | 10/2005 | |
| JP | 3128871 | U | | 1/2007 | |
| JP | 2007-229507 | A | | 9/2007 | |
| JP | 2008245714 | A | * | 10/2008 | ......... A61B 1/00149 |
| JP | 2012-121080 | A | | 6/2012 | |
| WO | WO-02070943 | A2 | * | 9/2002 | ........... G01N 29/225 |

OTHER PUBLICATIONS

Extended European Search Report dated Oct. 23, 2018 in European Patent Application No. 16768890.2, 6 pages.

Office Action dated Nov. 26, 2019 issued in corresponding Japanese Application No. 2017-508430, 8 pages.

* cited by examiner

MEDICAL OBSERVATION DEVICE, SURGICAL OBSERVATION DEVICE, AND MEDICAL OBSERVATION SYSTEM

TECHNICAL FIELD

The present disclosure relates to a medical observation device, a surgical observation device, and a medical observation system.

BACKGROUND ART

In recent years, support arm devices for assisting with surgery and examinations have come to be used in medical settings. For example, an optical observation device (observation device) in which a magnifying optical system for performing magnified observation of an extremely small portion of a surgical site of a patient is provided on a distal end of a support unit of a support arm device. When performing surgery using an optical observation device, an operator such as a doctor performs the surgery while directly observing the surgical site through an eyepiece provided with the magnifying optical system.

With such an observation device, various technologies for realizing better operability are being developed by devising arrangements and configurations of power transmission mechanisms such as gears that transmit the movement of components in the support unit. For example, Patent Literature 1 describes a stand device for holding medical optical equipment such as a magnifying optical system. This stand device includes a first link that is pivotally mounted to a holding unit by a first rotating joint, and a second link that is rotatably coupled to the first link via a second rotating joint. The second link supports a receiving unit that holds the medical optical equipment, with a third rotating joint of a section in front of the second link. The receiving unit has a front link, and this front link is coupled to the second rotating joint via a third link and a fourth link. The receiving unit and the fourth link are connected by a geared transmission device such that the orientation of the front link will not change when the first link moves.

According to the stand device described in Patent Literature 1, frictional surface contact with high internal friction is obtained by the receiving unit and the fourth link being connected via the geared transmission device. As a result, vibration of the receiving unit caused by shaking of the floor (building) where the stand device is arranged, for example, is significantly damped, so vibration of the medical observation equipment held by the stand device is able to be suppressed.

CITATION LIST

Patent Literature

Patent Literature 1: JP 2004-267774A

DISCLOSURE OF INVENTION

Technical Problem

Now in recent years, an electronic imaging observation device (observation device) has been proposed in which a microscope unit having a function that magnifies and captures an image of a surgical site is provided on a distal end of a support unit of such a medical observation device. In a case where surgery is performed using the electronic imaging observation device, an image of the surgical site captured by the microscope unit is displayed on a display device arranged in an operating room, and an operator performs surgery while looking at the image on the display device.

With this kind of electronic imaging observation device, the microscope unit and the distal end of the support unit to which the microscope unit is mounted are positioned near the surgical site. Therefore, if the structure near the distal end of the support unit is large, the workspace of the operator will be limited, which may make it difficult to perform a procedure smoothly. Also, with an electronic imaging observation device, the operator performs surgery while looking at an image on the display device arranged in the operating room, as described above, so the support unit may be positioned between the operator and the display device. Therefore, if the structure near the distal end of the support unit is large, the view of the operator looking at the display device may end up being blocked, which may hinder work by the operator from being performed smoothly.

In this way, there is a need for medical observation devices, particularly the support unit of electronic imaging observation devices, to be smaller in order for surgery and examinations to be performed more smoothly. However, until now, downsizing of the structure of the support unit of an electronic imaging observation device has not been sufficiently examined.

In particular, in recent years, an observation device realized in which an actuator is provided for each joint unit that forms a support unit, and movement of the support unit is realized by rotatably driving the joint units by the actuators, has been proposed. In such an observation device provided with actuators for the joint units, there is a concern that the size of the support unit will increase by an amount corresponding to the space that it takes to mount the actuators. That is, if an actuator is provided for each joint unit, it will be conceivably even more difficult to reduce the size of the support unit.

Therefore, the present disclosure proposes a new and improved medical observation device, surgical observation device, and medical observation system, in which the structure of a support unit is able to be made smaller.

Solution to Problem

According to the present disclosure, there is provided a medical observation device including: an imaging unit configured to capture an image of an object to be observed, and output a video signal; and a support unit configured with a plurality of arm units rotatably connected to each other via joint units, and configured to support the imaging unit. An actuator that applies driving force with respect to rotation about a rotational axis of at least one joint unit that defines an attitude of the imaging unit, among a plurality of the joint units that form the support unit, is provided. The at least one joint unit and the actuator are arranged separated from each other, and are connected to each other via a power transmission mechanism that transmits rotary movement between two rotational axes that are substantially orthogonal to each other.

In addition, according to the present disclosure, there is provided a surgical observation device including: a microscope unit configured to capture an image of an object to be observed, and output a video signal; and a support unit configured with a plurality of arm units rotatably connected to each other via joint units, and configured to support the microscope unit. An actuator that applies driving force with respect to rotation about a rotational axis of at least one joint unit that defines an attitude of the microscope unit, among a plurality of the joint units that form the support unit, is provided. The at least one joint unit and the actuator are arranged separated from each other, and are connected to each other via a power transmission mechanism that transmits rotary movement between two rotational axes that are substantially orthogonal to each other.

In addition, according to the present disclosure, there is provided a medical observation system including: an observation device configured to include an imaging unit that captures an image of an object to be observed and outputs a video signal, and a support unit which is configured with a plurality of arm units rotatably connected to each other via joint units, and which supports the imaging unit; and a display device configured to display an image of the object to be observed captured by the imaging unit, on the basis of the video signal. In the observation device, an actuator that applies driving force with respect to rotation about a rotational axis of at least one joint unit that defines an attitude of the imaging unit, among a plurality of the joint units that form the support unit, is provided, and the at least one joint unit and the actuator are arranged separated from each other, and are connected to each other via a power transmission mechanism that transmits rotary movement between two rotational axes that are substantially orthogonal to each other.

According to the present disclosure, at least one joint unit, among joint units capable of defining the attitude of a microscope unit, and an actuator that applies driving force to the at least one joint unit, are arranged apart from one another via a power transmission mechanism. The joint unit capable of defining the attitude of the microscope unit is typically often provided near the microscope unit, so by arranging at least one joint unit, among the joint units capable of defining the attitude of the microscope unit, and the actuator, separated from each other in this way, the structure near the microscope unit is able to be made even smaller.

Advantageous Effects of Invention

According to the present disclosure as described above, the structure of the support unit is able to be made even smaller. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
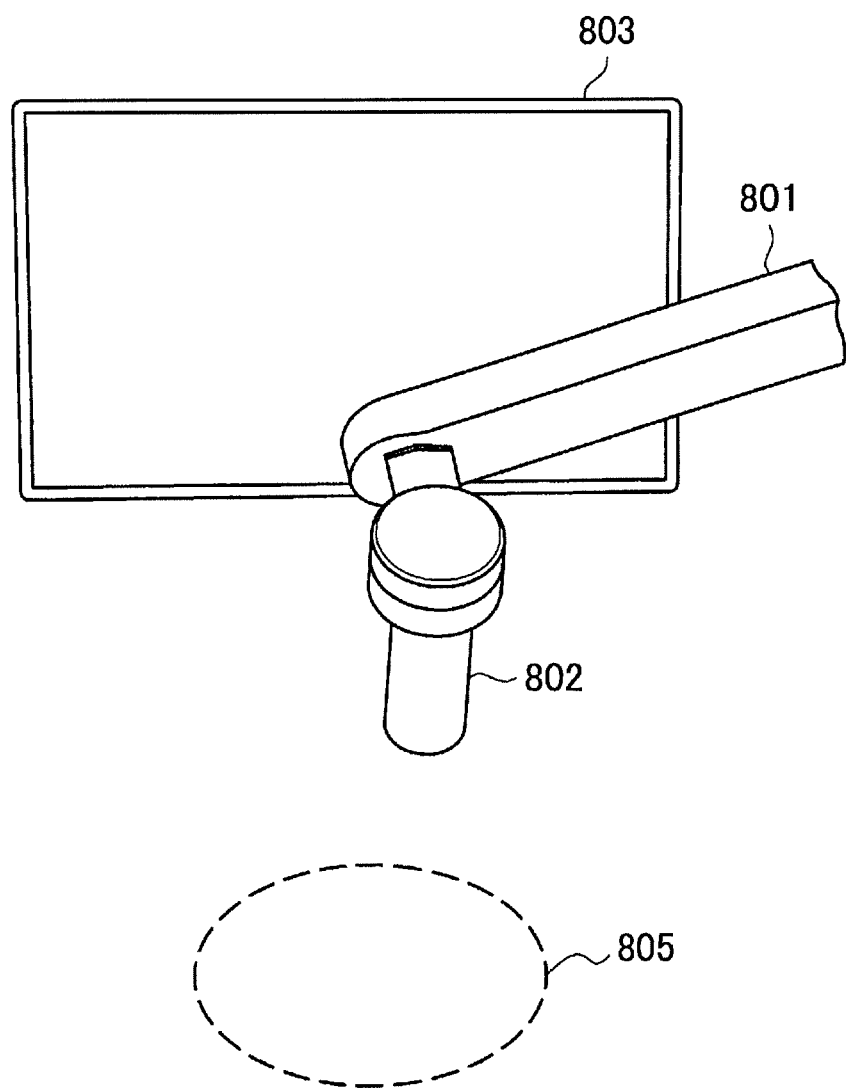
FIG. 1 is a view schematically illustrating a surgical situation in which an electronic imaging observation device is used.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that the description will be given in the following order.

1. Background of present disclosure
   1-1. Considerations regarding electronic imaging observation device
   1-2. Considerations regarding observation device having an actuator at a joint unit
2. First Embodiment
   2-1. Structure of observation system and observation device
   2-2. Structure of power transmission mechanism
   2-3. Modified example of actuator
3. Second Embodiment
   3-1. Structure of observation system and observation device
   3-2. Structure of power transmission mechanism
4. Comparison of first and second embodiments
5. Usage example
6. Supplemental remarks Note that in the following, the user who performs various operations on an observation device according to an embodiment of the present disclosure is designated the surgeon for the sake of convenience. However, this designation does not limit the user who uses the observation device, and the various operations on the observation device may also be executed by any user, such as another member of the medical staff.

1. Background of Present Disclosure

Before describing the structure of the observation device and the observation system according to a preferred embodiment of the present disclosure in detail, the inventors will first describe the background of the present disclosure in order to make the present disclosure clearer.

Note that in the following description, a unit for observing a surgical site, which is provided on an observation device, such as a microscope unit of an electronic imaging observation device, and a magnifying optical system of an optical observation device, will collectively be referred to as an observation unit.

(1-1. Considerations Regarding Electronic Imaging Observation Device)

As described above, in recent years, an electronic imaging observation device has been proposed in which a microscope unit having a function that magnifies and captures an image of a surgical site is provided on a distal end of a support unit of a medical observation device. In a case where surgery is performed using an electronic imaging observation device, an image of the surgical site captured by the microscope unit is displayed on a display device arranged in an operating room, and a surgeon performs surgery while looking at the image on the display device.

Figure 2:
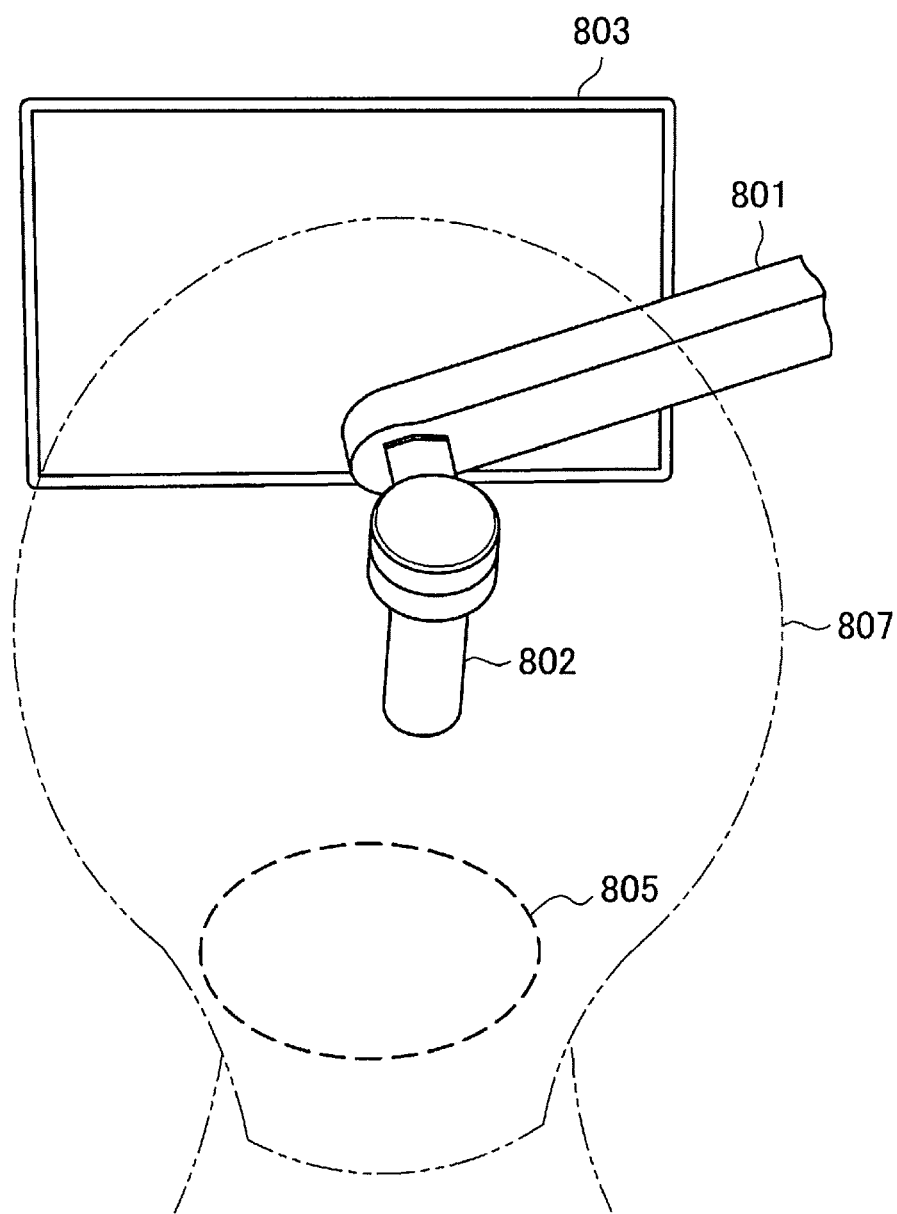
FIG. 2 is a view schematically illustrating a surgical situation in which an electronic imaging observation device is used.

FIG. 1 and FIG. 2 are views schematically illustrating a surgical situation in which an electronic imaging observation device is used. FIG. 1 schematically illustrates the positional relationships among a structure near a distal end of a support unit 801 of an observation device, a microscope unit 802 mounted to the distal end of the support unit 801, a display device 803 on which an image captured by the microscope unit 802 is displayed, and an image capture range 805 of the microscope unit 802, during surgery. A surgical site of the patient to be observed (i.e., where surgery is to be performed) is positioned in the image capture range 805.

As illustrated in FIG. 1, the microscope unit 802 can be positioned near the image capture range 805, i.e., near the surgical site. If the structure of the support unit 801 that supports the microscope unit 802 is large in order for the surgeon to perform various procedures on the surgical site, there may be interference between the hands of the surgeon performing the procedure and the support unit 801, which may hinder work from being performed smoothly.

On the other hand, the surgeon performs the surgery while looking at the image displayed on the display device 803, as described above. In FIG. 2, the head of the surgeon 807 is shown added, in a simulated manner, to the structure illustrated in FIG. 1. Taking into account the positional relationships among the support unit 801, the microscope unit 802, the display device 803, the image capture range 805, and the surgeon 807, the surgeon 807 looks at the display device 803 over the support unit 801 and the microscope unit 802, as illustrated in FIG. 2. Therefore, if the structure of the support unit 801 is large, the field of view of the surgeon looking at the display device 803 may end up being obstructed by the support unit 801, which may hinder work by the surgeon 807 from being performed smoothly.

In this way, in order to ensure the workspace and field of view of the surgeon 807, the structure of the support unit 801, particularly the structure near the distal end of the support unit 801, in the electronic imaging observation device needs to be made smaller. Although there may also be a need to similarly reduce the size of an optical observation device, it is assumed that with an electronic imaging observation device, the surgeon 807 performs surgery while looking at the display device 803 as described above, so such a need to reduce the size of the support unit 801 is even greater from the viewpoint of ensuring the field of view of the surgeon 807.

(1-2. Considerations Regarding Observation Device Having an Actuator at a Joint Unit)

On the other hand, in recent years, an observation device in which an actuator is provided for each joint unit that forms a support unit has been proposed. In this kind of observation device having actuators at the joint units, operation of the support unit is controlled so that an observation unit mounted to the distal end of the support unit assumes a desired position and attitude, by the driving of the actuators provided at the joint units being controlled by any of a variety of types of control methods, such as position control or force control, for example.

Here, with the observation device, rotational axes in three directions orthogonal to each other for defining the attitude of the observation unit are typically provided for the observation unit, so that a surgical site can be observed from any angle by the observation unit. Here, the attitude of the microscope unit refers to the orientation of the optical axis of the microscope unit with respect to the object being observed. Therefore, considering that actuators are provided for the joint units corresponding to these rotational axes, the structure near the observation unit of the support unit may end up being relatively large because the actuators are arranged near the observation unit.

Figure 3:
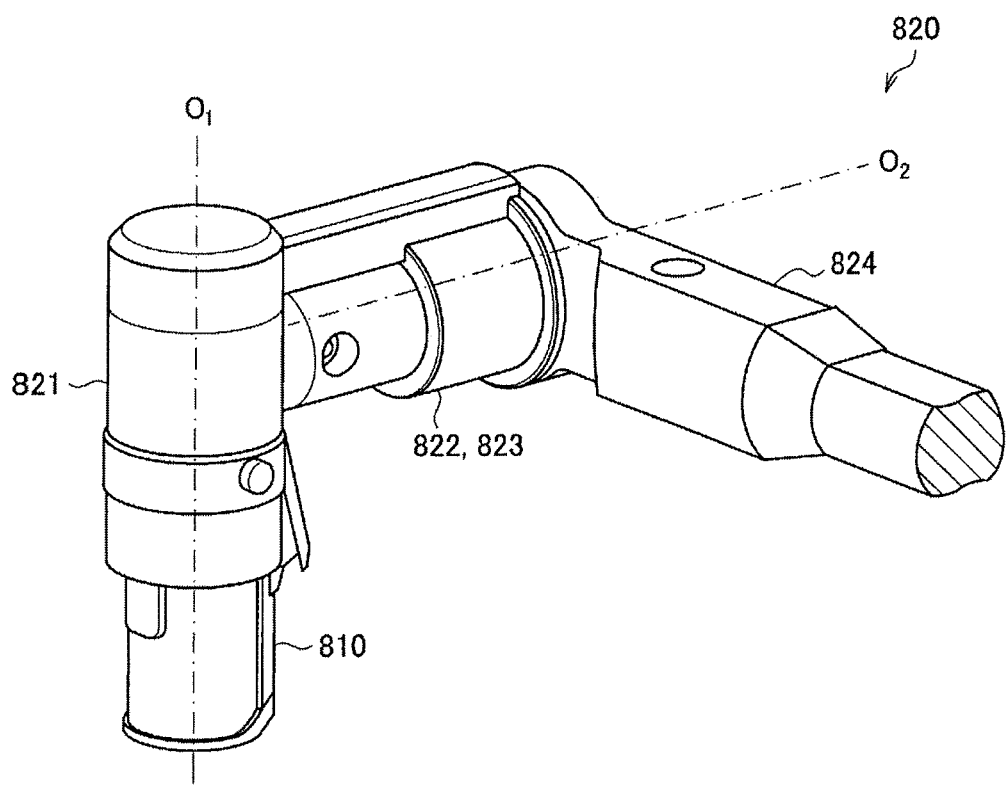
FIG. 3 is a view illustrating an example of a typical configuration of a support unit provided with an actuator.

An example of a typical configuration of a support unit provided with an actuator is illustrated in FIG. 3. FIG. 3 is a view illustrating an example of a typical configuration of a support unit provided with an actuator. Note that in the description below, the region of the support unit of the observation device that is near the observation unit may also be referred to as a distal end region for convenience.

In FIG. 3, only the structure of the distal end region of a typical support unit 820 provided with an actuator is extracted and illustrated. Referring to FIG. 3, a microscope unit 810, a first joint unit 821 that holds the microscope unit 810 in a manner that enables the microscope unit 810 to rotate about a first axis $O_1$ that is a rotational axis substantially parallel to the image capturing direction (optical axis direction) of the microscope unit 810, a first arm unit 822 that extends in a direction substantially orthogonal to the first axis $O_1$ from a side surface of the first joint unit 821, a second joint unit 823 that holds the first joint unit 821 in a manner that enables the first joint unit 821 to rotate about a second axis $O_2$ that is a rotational axis substantially parallel to the direction in which the first arm unit 822 extends, and a second arm unit 824 that is fixed at one end to a proximal end side of the second joint unit 823 and extends in a direction orthogonal to both the first axis $O_1$ and the second axis $O_2$, are illustrated as a configuration example of the distal end region of the typical support unit 820. In the illustrated example, the first arm unit 822 and the second joint unit 823 are configured as an integrated member.

Also, although not illustrated, a third joint unit that holds the second arm unit 824 in a manner that enables the second arm unit 824 to rotate about a third axis $O_3$ that is a rotational axis substantially parallel to the direction in which the second arm unit 824 extends, can be provided on the proximal end side of the second arm unit 824. The orientation of the image captured by the microscope unit 810 is controlled by controlling the rotation about the first axis $O_1$. Also, the attitude of the microscope unit 810 is controlled by controlling the rotation about the second axis $O_2$ and the rotation about the third axis $O_3$. That is, the second axis $O_2$ and the third axis $O_3$ can be rotational axes that define the attitude of the microscope unit 810.

Actuators that apply driving force with respect to rotation about the first axis $O_1$ and the second axis $O_2$ are provided inside the first joint unit 821 and the second joint unit 823, respectively. Note that although the other joint units are not illustrated in FIG. 3, actuators can similarly be provided for the other joint units in the support unit 820. The first joint unit 821 and the second joint unit 823 are naturally larger, by the amount of the actuators, than the first joint unit 821 and the second joint unit 823 would be if the actuators were not provided. In this way, with the typical support unit 820, the structure of the distal end region tends to become larger as a result of providing the actuators.

Above, the inventors have described the considered content regarding an electronic imaging observation device, and an observation device having actuators at joint units. The results considered by the inventors will now be summarized.

As described above, in an electronic imaging observation device, the structure of the support unit, particularly the structure of the distal end region of the support unit, needs to be made smaller in order to ensure the workspace and field of view of the surgeon. On the other hand, as described with reference to FIG. 3, with a structure of a typical support unit of an observation device having actuators at joint units, the structure of the distal end region of the support unit tends to end up becoming larger as a result of providing the actuators. Therefore, assuming a case in which surgery is performed using an electronic imaging observation device having actuators at joint units of a support unit, it is conceivable that it will be difficult to ensure the workspace and field of view of the surgeon.

However, until now, downsizing of the structure of the distal end region of the support unit of an observation device having actuators in joint units of a support unit has not been sufficiently examined. For example, making the actuator itself smaller is one conceivable way to make the structure of the distal end region of the support unit smaller. However, typically, the size of a motor and a reducer and the like that form the actuator can be determined in accordance with the output required for the actuator, i.e., the driving force required for rotation about the rotational axes. Therefore, there is a limit as to how small the actuator can be, in order to maintain a predetermined output for making the support unit perform a desired operation.

In view of the situation described above, the inventors have conceived a preferred embodiment of the present disclosure described below, as a result of intense study of technology for making the structure of the distal end region of a support unit smaller, in an observation device having an actuator in a joint unit of the support unit. Hereinafter, a preferable embodiment of the present disclosure conceived by the inventors will be described.

2. First Embodiment (2-1. Structure of Observation System and Observation Device)

Figure 4:
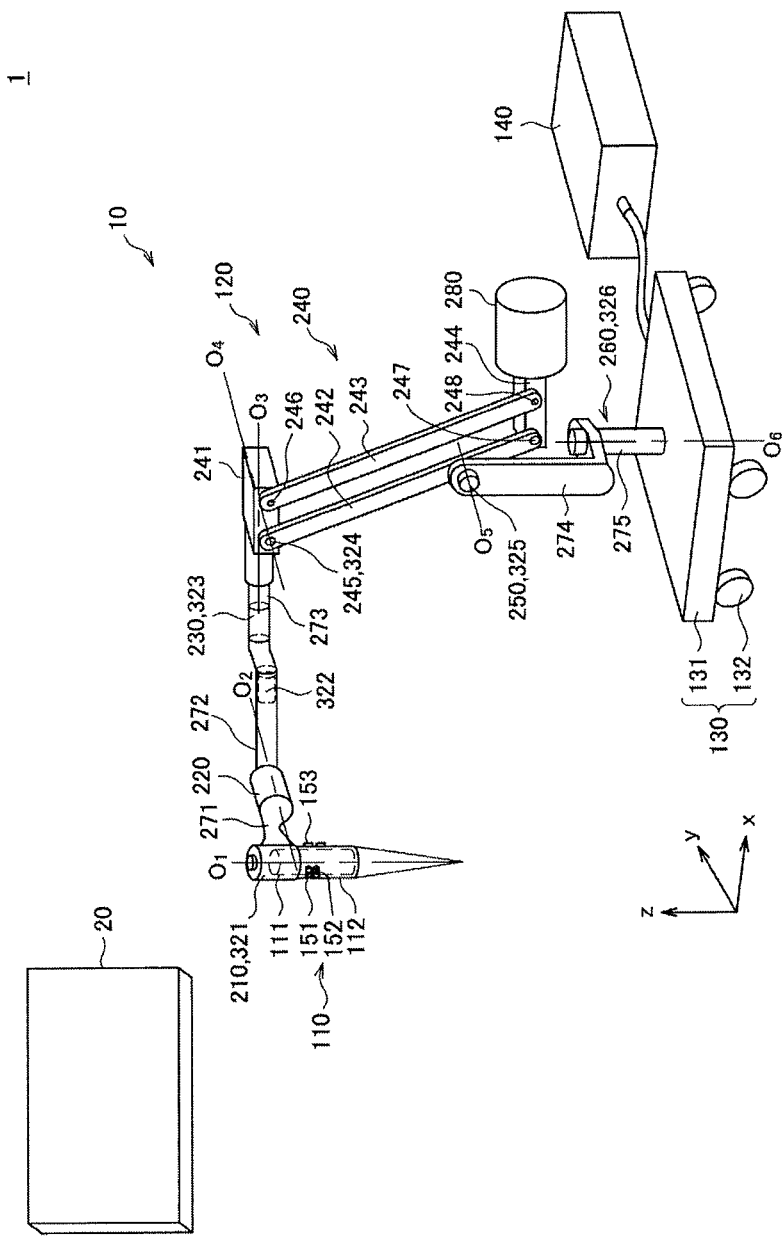
FIG. 4 is a view illustrating a configuration example of an observation system according to a first embodiment.

The structure of an observation system according to a first embodiment of the present disclosure, and an observation device that forms the observation system, will be described with reference to FIG. 4. FIG. 4 is a view illustrating a configuration example of the observation system according to the first embodiment.

Referring to FIG. 4, the observation system 1 according to the first embodiment includes an observation device 10 that supports a microscope unit 110 and captures an image of a surgical site of a patient with the microscope unit 110, and a display device 20 that displays the image of the surgical site captured by the observation device 10. During surgery, the surgeon observes the surgical site and performs various procedures on the surgical site, while referring to the image captured by the observation device 10 and displayed on the display device 20.

(Display Device)

As discussed above, the display device 20 displays the image of the patient's surgical site captured by the observation device 10. The display device 20 is installed in a location visible to the surgeon, such as on a wall of the operating room, for example. The type of the display device 20 is not particularly limited, and any of various known types of display devices may be used as the display device 20, such as a cathode ray tube (CRT) display device, a liquid crystal display device, a plasma display device, or an electroluminescence (EL) display device. Additionally, the display device 20 is not necessarily required to be installed inside the operating room, and may also be mounted onboard a device used by being worn on the surgeon's body, such as a head-mounted display (HMD) or an eyeglasses-type wearable device.

Note that, as will be described later, in a case in which an imaging unit 111 of the microscope unit 110 of the observation device 10 is configured as a stereo camera, or such that high-resolution imaging is possible, a display device 20 capable of 3D display or capable of displaying an image with high resolution may be used accordingly.

(Observation Device)

The observation device 10 is equipped with a microscope unit 110 for performing magnified observation of the patient's surgical site, a support unit 120 (arm unit 120) that supports the microscope unit 110, a base unit 130 to which one end of the support unit 120 is connected and which supports the microscope unit 110 and the support unit 120, and a control device 140 that controls the operation of the observation device 10. The observation device 10 is a medical observation device for magnifying and observing, with the microscope unit 110, a portion to be treated by the surgeon during surgery or an examination.

(Base Unit)

The base unit 130 is a base of the observation device 10 that supports the microscope unit 110 and the support unit 120. The base unit 130 includes a platform 131 having a planar shape, and multiple casters 132 provided on the bottom face of the platform 131. One end of the support unit 120 is connected to the top face of the platform 131, while the microscope unit 110 is connected to the other end of the support unit 120 extending from the platform 131 (the distal end). Also, the observation device 10 is in contact with the floor through the casters 132, and is configured to be movable across the floor by the casters 132.

Note that in the following description, the direction perpendicular to the floor on which the observation device 10 is installed is defined to be the z-axis direction. The z-axis direction is also called the up-and-down direction or the vertical direction. Additionally, the two mutually orthogonal directions to the z-axis direction are defined to be the x-axis direction and the y-axis direction. The direction parallel to the x-y plane is also called the horizontal direction.

(Microscope Unit)

The microscope unit 110 is made up of a microscope body for performing magnified observation of the patient's surgical site. In the illustrated example, the optical axis direction of the microscope unit 110 is approximately aligned with the z-axis direction. The microscope unit 110 has a configuration corresponding to a microscope unit of the electronic imaging type, and is made up of a barrel unit 112 having an approximately cylindrical shape, and an imaging unit 111 provided inside the barrel unit 112. Additionally, the imaging unit 111 is made up of an optical system such as an objective lens and a zoom lens, and an image sensor that captures an image of a subject (namely, the surgical site) with light passing through the optical system.

The aperture on the bottom end of the barrel unit 112 is provided with a cover glass for protecting the imaging unit 111. A light source is also provided inside the barrel unit 112, and during image capture, the subject is irradiated with illuminating light radiating from the light source through the cover glass. Of this illuminating light, the light reflecting back from the subject (observation light) is incident on the imaging unit 111 via the cover glass, and as a result, a signal indicating the image of the surgical site (video signal) is acquired by the imaging unit 111.

For the microscope unit 110, it is sufficient to apply a configuration corresponding to any of various known types of electronic imaging microscope units, and for this reason a detailed description thereof will be reduced or omitted herein. For example, any of various known types of image sensors may be applied as the image sensor of the imaging unit 111, such as a charge-coupled device (CCD) sensor or a complementary metal-oxide-semiconductor (CMOS) sensor. Additionally, the imaging unit 111 may also be configured as a stereo camera equipped with a pair of image sensors. Also, any of various known types of configurations may be applied to the optical system of the imaging unit 111. Furthermore, any of various types of functions typically provided in electronic imaging microscope units, such as an autofocus (AF) function and an optical zoom function, may be provided onboard the imaging unit 111.

Also, the imaging unit 111 may be configured such that high-resolution imaging, such as 4K or 8K imaging, for example, is possible. Having the imaging unit 111 be configured such that high-resolution imaging is possible enables an image to be displayed on the display device 20 with a large screen of 50 inches or more, for example, while ensuring a predetermined resolution (e.g., Full, HD image quality), so visibility by the surgeon improves. Also, the predetermined resolution is able to be ensured even when an image is displayed after having been suitably magnified by an electronic zoom function. Therefore, there is no longer a need for the optical zoom function in the microscope unit 110, so the optical system of the microscope unit 110 is able to be simpler. Consequently, the microscope unit 110 can be made smaller.

The video signal acquired by the microscope unit 110 is transmitted to the control device 140. Various kinds of image processing, such as gamma correction, white balance adjustment, and magnification and inter-pixel correction relating to the electronic zoom function and the like, for example, are performed on the video signal in the control device 140. With this image processing, various kinds of image processing typically performed to display an image may be performed. The video signal that has undergone the various kinds of image processing is transmitted to the display device 20 provided in the operating room, and an image of the surgical site is appropriately magnified at the desired magnification by the optical zoom function and/or the electronic zoom function, for example, and displayed on the display device 20. Note that communication between the control device 140 and the display device 20 may be realized by any of various well-known wired or wireless methods.

Note that a processing circuit for performing the above image processing may be provided in the microscope unit 110, and the above image processing may be performed by the processing circuit of the microscope unit 110, without being performed by the control device 140. In this case, image information after suitable image processing has been performed in the processing circuit onboard the microscope unit 110 may be transmitted from the microscope unit 110 to the display device 20 provided in the operating room. Also, in this case, the communication between the microscope unit 110 and the display device 20 may be realized by any of various known wired or wireless methods.

The outer surface of the microscope unit 110 is provided with various types of switches for controlling the operation of the microscope unit 110. For example, the microscope unit 110 is provided with a zoom switch 151 (zoom SW 151) and a focus switch 152 (focus SW 152) for adjusting the image capture parameters of the microscope unit 110, as well as an operating mode toggle switch 153 (operating mode toggle SW 153) for toggling the operating mode of the support unit 120.

The surgeon, by operating the zoom SW 151 and the focus SW 152, is able to adjust the magnification and the focal length of the microscope unit 110, respectively. Also, by operating the operating mode toggle SW 153, the surgeon is able to toggle the operating mode of the support unit 120 between a locked mode and a free mode.

Herein, the locked mode is an operating mode in which the position and the attitude of the microscope unit 110 are locked by using a brake to restrain rotation about each rotation axis provided in the support unit 120. The free mode is an operating mode in which the brake is released, thereby allowing free rotation about each rotation axis provided in the support unit 120, and enabling the surgeon to adjust the position and the attitude of the microscope unit 110 with direct operations. Herein, direct operations mean operations in which the surgeon grips the microscope unit 110 with his or her hand, for example, and directly moves the microscope unit 110. For example, the operating mode of the support unit 120 becomes the free mode while the surgeon is pressing the operating mode toggle SW 153, and the operating mode of the support unit 120 becomes the locked mode while the surgeon releases his or her hand from the operating mode toggle SW 153.

Note that these switches are not necessarily required to be provided on the microscope unit 110. In the first embodiment, it is sufficient for the observation device 10 to be provided with a mechanism for accepting operating input having functions similar to these switches, and the specific configuration of such a mechanism is not limited. For example, these switches may also be provided on another section of the observation device 10. As another example, an input device such as a remote control, a foot switch or the like may be used, and commands corresponding to these switches may be input into the observation device 10 remotely.

Also, although the barrel unit 112 of the microscope unit 110 is illustrated as a simple cylindrically-shaped member in FIG. 4 for the sake of simplicity, the barrel unit 112 may also be provided with a grip unit gripped by the surgeon. Such a grip unit may be realized by having a structure such as a handle to be gripped by the surgeon be formed around the outer circumference of the barrel unit 112. Alternatively, such a grip unit may be realized by having the shape of the barrel unit 112 be formed into a shape that is gripped easily by the surgeon. For example, as described above, when in the free mode, operations of moving the microscope unit 110 with the surgeon gripping the barrel unit 112 directly in hand may be anticipated. At this point, since the surgeon performs an operation of moving the microscope unit 110 while pressing the operating mode toggle SW 153, the shape of the barrel unit 112 and the placement of the operating mode toggle SW 153 may be determined appropriately with consideration for operability by the surgeon while in the free mode. In addition, the placement of the zoom SW 151 and the focus SW 152 may be determined appropriately with similar consideration for operability by the surgeon.

(Control Device)

The control device 140 may be a processor, such as a central processing unit (CPU) or a digital signal processor (DSP), for example, or a control board on which these processors are mounted together with components such as memory. By executing computational processing according to a predetermined program, the control device 140 controls the operation of the observation device 10. Various functions of the control device 140 are realized by the processor that forms the control device 140 executing calculation processes in accordance with a predetermined program.

For example, the control device 140 controls the operation of the support unit 120 by controlling the rotation angle of each joint unit, which is accomplished by controlling the driving of actuators 321 to 326 provided for the joint units (a first joint unit 210 to a sixth joint unit 260) that form the support unit 120, described later. As will be described later, an encoder for detecting the rotation angle of each joint unit, and a torque sensor that detects torque applied to each joint unit, are provided in each of the actuators 321 to 326. The control device 140 ascertains the current state (position, attitude, and speed, etc.) of the support unit 120 on the basis of detection values from these encoders and torque sensors, and is able to calculate a control amount (e.g., rotary torque if the control method is force control) of each joint unit for realizing the operation of the support unit 120 dictated by the surgeon, on the basis of the ascertained state of the support unit 120. The support unit 120 is controlled by driving the joint units in accordance with the control amount.

The operation of the support unit 120 is suitably controlled by force control. For example, the operation of the support unit 120 can be controlled by force control, such that the support unit 120 moves in the direction of the force applied to the support unit 120, in response to a direct operation by the surgeon (an operation in which the surgeon grips the microscope unit 110 with a hand, for example, and directly moves the microscope unit 110). By controlling the operation of the support unit 120 to execute this kind of a so-called power assist operation, the surgeon is able to intuitively move the support unit 120 with less force, so operability by the surgeon improves. However, the control method of the support unit 120 is not particularly limited. The operation of the support unit 120 may be controlled by any of various control methods such as position control, for example. If the operation of the support unit 120 is controlled by position control, the observation device 10 can be provided with an input device such as a controller for operating the support unit 120. Any of various known methods may be used as the specific control method of the support unit 120, so a detailed description of the control method will be omitted.

For example, the control device 140 includes a function of toggling the operating mode of the support unit 120 discussed earlier by controlling the driving of the brake provided in each joint unit of the support unit 120 in response to operating input performed by the surgeon via the above operating mode toggle SW 153. As another example, the control device 140 includes a function of appropriately driving the optical system in the imaging unit 111 of the microscope unit 110 to adjust the magnification and the focal length of the microscope unit 110 in response to operating input performed by the surgeon via the above zoom SW 151 and focus SW 152. Also, the control device 140 controls the driving of the image sensor mounted to the imaging unit 111 of the microscope unit 110, and controls the timing of the start and end of image capture, for example. Also, the control device 140 has a function of performing various kinds of image processing on the video signal acquired by the microscope unit 110, and displaying an image based on the processed video signal on the display device 20. In addition, the control device 140 may have various functions provided in a control device of a typical observation device.

Here, communication among the various components of the observation device 10 (for example, communication between the microscope unit 110 and the control device 140, and communication between the control device 140 and the actuators 321 to 326 of the joint units 210 to 260 of the support unit 120, described later, and the like) is performed by wire over a cable, for example. The cable extends between the control device 140 and the joint units 210 to 260, and between the control device 140 and the microscope unit 110, so if the cable is exposed to the outside, it may obstruct the workspace and field of view of the surgeon. Therefore, in the first embodiment, the cable preferably extends inside the support unit 120. As a result, a situation in which the workspace and field of view of the surgeon is obstructed by the cable is able to be avoided, so convenience to the surgeon improves.

Note that in the illustrated example, the control device 140 is provided as a separate configuration from the microscope unit 110, the support unit 120, and the base unit 130, and is connected to the base unit 130 by a cable. However, the first embodiment is not limited to such an example. For example, a processor, a control board, or the like that realizes functions similar to the control device 140 may also be disposed inside the base unit 130. Additionally, by incorporating a processor, a control board, or the like that realizes functions similar to the control device 140 into the microscope unit 110 internally, the control device 140 and the microscope unit 110 may be configured in an integrated manner. Alternatively, functions similar to the functions of the control device 140 may be realized by a processor or a control board or the like being arranged in each joint unit that forms the support unit 120, and having these plurality of processors or control boards or the like work together.

(Support Unit)

The support unit 120 holds the microscope unit 110 and moves the microscope unit 110 three-dimensionally, as well as fixes the position and attitude of the microscope unit 110 after the microscope unit 110 has been moved. In the first embodiment, the support unit 120 is configured as a balance arm that has six degrees of freedom. However, the first embodiment is not limited to this example. The support unit 120 may also be configured to have another different number of degrees of freedom. By configuring the support unit 120 as a balance arm and having the moments of the microscope unit 110 and the support unit 120 be balanced on the whole, the surgeon is able to move the microscope unit 110 with such a small force that it seems as though the microscope unit 110 is weightless, in a direct operation.

The support unit 120 has six rotational axes (a first axis $O_1$, a second axis $O_2$, a third axis $O_2$, a fourth axis $O_4$, a fifth axis $O_5$, and a sixth axis $O_6$) corresponding to the six degrees of freedom. In the present specification, portions that form the rotational axes and rotatably connect the members will be referred to as joint units for descriptive purposes. For example, a joint unit can be formed by a bearing, and a shaft rotatably inserted into the bearing or the like. A parallelogram link mechanism 240, described later, can also be regarded as a single joint unit.

The support unit 120 includes a first joint unit 210, a second joint unit 220, a third joint unit 230, a fourth joint unit 240, a fifth joint unit 250, and a sixth joint unit 260, which correspond to the rotational axes, a first arm unit 271, a second arm unit 272, a third arm unit 273, a fourth arm unit 274, and a fifth arm unit 275, which are rotatably connected together by the first joint unit 210 to the sixth joint unit 260, and a counterweight 280 for balancing the moments of the microscope unit 110 and the support unit 120 on the whole. However, the fourth joint unit 240 corresponds to the parallelogram link mechanism 240.

Note that in the description below, when describing the structure of the support unit 120, the side on which the microscope unit 110 is provided will also be referred to as the distal end side or the distal end portion or the like, and the side near the base unit 130 will also be referred to as the proximal end side or the proximal end portion or the like.

The first joint unit 210 has a generally cylindrical shape, and is connected to the proximal end portion of the barrel unit 112 of the microscope unit 110 such that the central axis of the first joint unit 210 is substantially coincident with the central axis of the barrel unit 112 of the microscope unit 110. The first joint unit 210 rotatably supports the microscope unit 110, with the direction substantially coincident with the optical axis of the microscope unit 110 as the rotational axis direction (the direction of the first axis $O_1$). In the example illustrated in FIG. 1, the first axis $O_1$ is provided as a rotational axis that is substantially parallel to a z-axis. The orientation of the image captured by the microscope unit 110 is adjusted by rotating the microscope unit 110 about the first axis $O_1$ by the first joint unit 210.

Note that in the illustrated example, a portion of the imaging unit 111 of the microscope unit 110 is housed inside a generally cylindrical case that forms the first joint unit 210. That is, the microscope unit 110 and the first joint unit 210 are configured as an integrated member. However, the first embodiment is not limited to this example. The first joint unit 210 and the microscope unit 110 may also be configured as separate members.

A distal end of the first arm unit 271 that extends in a direction substantially perpendicular to the first axis $O_1$ is connected to the first joint unit 210. Also, the second joint unit 220 that rotatably supports the first arm unit 271, with a direction substantially parallel to the direction in which the first arm unit 271 extends as the rotational axis direction (the direction of the second axis $O_2$), is provided on a proximal end of the first arm unit 271. The second axis $O_2$ is a rotational axis that is substantially perpendicular to the first axis $O_1$, and is provided as a rotational axis that is substantially parallel to the y-axis in the example illustrated in FIG. 1. The position in the x-axis direction of the microscope unit 110 is adjusted by rotating the microscope unit 110 and the first arm unit 271, with the second axis $O_2$ as the rotational axis, by the second joint unit 220.

A distal end of the second arm unit 272 that extends in a direction substantially perpendicular to both the first axis $O_1$ and the second axis $O_2$ is connected to the second joint unit 220. The third joint unit 230 that rotatably supports the second arm unit 272, with a direction substantially parallel to the direction in which the second arm unit 272 extends as the rotational axis direction (the direction of the third axis $O_3$), is provided on a proximal end of the second arm unit 272. Note that at this time, the second arm unit 272 and the third joint unit 230 are connected in a state in which the central axes of the second arm unit 272 and the third joint unit 230 are offset, as illustrated in the drawings. That is, the connected portion of the second arm unit 272 and the third joint unit 230 forms a so-called crank shape.

The third axis $O_3$ is a rotational axis that is substantially perpendicular to both the first axis $O_1$ and the second axis $O_2$, and is provided as a rotational axis that is substantially parallel to the x-axis in the example illustrated in FIG. 1. The position in the y-axis direction of the microscope unit 110 is adjusted by rotating the microscope unit 110, the first arm unit 271, and the second arm unit 272, with the third axis $O_3$ as the rotational axis, by the third joint unit 230.

In this way, the support unit 120 is configured such that the attitude of the microscope unit 110 is controlled by controlling the rotation about both the second axis $O_2$ and the third axis $O_3$. That is, the second joint unit 220 and the third joint unit 230 can be joints that define the attitude of the microscope unit 110.

A distal end of the third arm unit 273 that extends in a direction substantially parallel to the third axis $O_3$ is connected to the third joint unit 230. Also, the distal end on the upper side of the parallelogram link mechanism 240 is connected to the proximal end of the third arm unit 273.

The parallelogram link mechanism 240 has four arms (arms 241, 242, 243, and 244) arranged in the shape of a parallelogram, and four rotating parts (rotating parts 245, 246, 247, and 248) each provided in a position corresponding to substantially a vertex of the parallelogram. The rotating parts 245 to 248 are mechanisms that rotatably connect two members together.

The distal end of the arm 241 that extends in a direction substantially parallel to the third axis $O_3$ is connected to the proximal end of the third arm unit 273. The rotating part 245 is provided near the distal end of the arm 241, and the rotating part 246 is provided near the proximal end of the arm 241. The distal ends of the arms 242 and 243 are connected to the rotating parts 245 and 246, respectively, in a manner that enables the distal ends of the arms 242 and 243 to rotate about rotational axes (the fourth axis $O_4$) that are substantially perpendicular to the direction in which the arm 241 extends, and substantially parallel to each other. Moreover, the rotating parts 247 and 248 are provided on proximal ends of the arms 242 and 243, respectively. A distal end and a proximal end of the arm 244 are connected to these rotating parts 247 and 248, respectively, in a manner able to rotate about the fourth axis $O_4$ and substantially parallel to the arm 241.

In this way, the four rotating parts 245 to 248 that form the parallelogram link mechanism 240 have rotational axes (the fourth axis $O_4$) in substantially the same direction that are substantially parallel to each other, and operate in conjunction with each other about the fourth axis $O_4$. In the example illustrated in FIG. 1, the fourth axis $O_4$ is provided as a rotational axis that is substantially parallel to the y-axis. That is, the parallelogram link mechanism 240 is configured to have a plurality of rotating portions that are arranged in different positions from each other, and that rotate in conjunction with each other on rotational axes that are in the same direction, such that the parallelogram link mechanism 240 behaves as a transmission mechanism that transmits operation at one end to the other end.

The fifth joint unit 250 that rotatably supports the parallelogram link mechanism 240, with a direction perpendicular to the direction in which the arm 242 extends as the rotational axis direction (the direction of the fifth axis $O_5$), is provided on a portion a predetermined distance away from the proximal end of the arm 242. The fifth axis $O_5$ is a rotational axis that is substantially parallel to the fourth axis $O_4$, and is provided as a rotational axis that is substantially parallel to the y-axis in the example illustrated in FIG. 1. A distal end of the fourth arm unit 274 that extends in the z-axis direction is connected to the fifth joint unit 250. According to this configuration, the structure on the distal end side of the parallelogram link mechanism 240 rotates with respect to the fourth arm unit 274, with the fifth axis $O_5$ as the rotational axis, via the fifth joint unit 250.

The fourth arm unit 274 is generally L-shaped, and the proximal end side of the fourth arm unit 274 is bent so as to be substantially parallel to the floor. The sixth joint unit 260 capable of rotating the fourth arm unit 274 about a rotational axis (the sixth axis $O_6$) parallel to the vertical direction is connected to a surface of the fourth arm unit 274 that is substantially parallel to the floor.

In the illustrated example, the sixth joint unit 260 is integrally formed with the fifth arm unit 275 that extends in the vertical direction. That is, the distal end of the fifth arm unit 275 is connected to a surface of the proximal end of the fourth arm unit 274 that is substantially parallel to the floor. Also, the proximal end of the fifth arm unit 275 is connected to top face of the platform 131 of the base unit 130. According to this configuration, the structure on the distal end side of the fourth arm unit 274 rotates with respect to the base unit 130, with the sixth axis $O_6$ as the rotational axis, via the sixth joint unit 260.

The arm 244 that forms the lower side of the parallelogram link mechanism 240 is formed longer than the arm 241 that forms the upper side of the parallelogram link mechanism 240, and the end of the arm 242 that is positioned diagonally opposite the portion of the parallelogram link mechanism 240 to which the third joint unit 230 is connected extends to the outside of the parallelogram link mechanism 240. The counterweight 280 is provided on the extending end of the arm 244. The mass and placement position of the counterweight 280 are adjusted such that the rotation moment generated about the fourth axis $O_4$ and the rotation moment generated about the fifth axis $O_5$ are able to cancel each other out by the mass of the structures (i.e., the microscope unit 110, the first joint unit 210, the second joint unit 220, the third joint unit 230, the first arm unit 271, the second arm unit 272, the third arm unit 273, and the parallelogram link mechanism 240) that are arranged to the distal end side of the counterweight 280 itself.

Also, the placement position of the fifth joint unit 250 is adjusted such that the center of gravity of each of the structures arranged to the distal end side of the fifth joint unit 250 is positioned on the fifth axis $O_5$. Moreover, the placement position of the sixth joint unit 260 is adjusted such that the center of gravity of each of the structures arranged to the distal end side of the sixth joint unit 260 is positioned on the sixth axis $O_6$. By having the mass and placement position of the counterweight 280, the placement position of the fifth joint unit 250, and the placement position of the sixth joint unit 260 configured in this way, the support unit 120 can be configured as a balance arm in which the moments of the microscope unit 110 and the support unit 120 are balanced on the whole.

Here, in the first embodiment, the rotation of the members about the rotational axes (the first axis $O_1$ to the sixth axis $O_6$) of the support unit 120 is able to be driven by actuators. Therefore, the actuators 321, 322, 323, 324, 325, and 326 that apply driving force with respect to rotation about the rotational axes are provided in the first joint unit 210 to the sixth joint unit 260, respectively.

In the illustrated example, the actuators 321, 323, 325, and 326 are provided inside the first joint unit 210, the third joint unit 230, the fifth joint unit 250, and the sixth joint unit 260, with respect to the first axis $O_1$, the third axis $O_3$, the fifth axis $O_5$, and the sixth axis $O_6$, respectively. Also, the four rotating parts (rotating parts 245 to 248) of the parallelogram link mechanism 240 that corresponds to the fourth joint unit 240 rotate in conjunction with each other, so an actuator 324 is provided in any one of these rotating parts 245 to 248. In the illustrated example, the actuator 324 is provided in the rotating part 245 (strictly speaking, the actuator 324 can be provided inside the arm 241, but this is not illustrated in FIG. 4 for simplicity). However, the first embodiment is not limited to this example. The actuator 324 may also be provided in any one of the other rotating parts 246 to 248 of the parallelogram link mechanism 240.

On the other hand, an actuator 322 is provided at a position away from the second joint unit 220, with respect to the second axis $O_2$, as illustrated in the drawings. More specifically, the actuator 322 is arranged in the proximal end portion of the second arm unit 272, and the second joint unit 220 is arranged in the distal end portion of the second arm unit 272. Also, the second joint unit 220 and the actuator 322 are connected by a power transmission mechanism (not illustrated) provided inside the second arm unit 272, and the driving force of the actuator 322 is transmitted to the second joint unit 220 by the power transmission mechanism. In the first embodiment, the second joint unit 220 and the actuator 322 that applies driving force with respect to rotation about the second axis $O_2$ of the second joint unit 220 are arranged separated from each other via the power transmission mechanism in this way. According to this configuration, the actuator 322 is able to be arranged in a position farther away from the second joint unit 220, so the second joint unit 220, i.e., the structure of the distal end region, is able to be smaller. Accordingly, workspace for the surgeon and the field of view of the surgeon are able to be better ensured.

Also, in the first embodiment, at this time, a power transmission mechanism capable of transmitting rotary movement between two rotational axes that are substantially orthogonal to each other is used as the power transmission mechanism that connects the second joint unit 220 and the actuator 322. As a result, the actuator 322 is able to be arranged such that the second axis $O_2$ that is the rotational axis of the second joint unit 220 and the driving axis (hereinafter, also referred to as the rotational axis for convenience) of the actuator 322 are orthogonal to each other. That is, the actuator 322 can be arranged such that the rotational axis of the actuator 322 faces a direction that is substantially parallel to the direction in which the second arm unit 272 extends. As a result, the amount that the actuator 322 protrudes in a direction substantially orthogonal to the direction in which the second arm unit 272 extends is able to be suppressed.

As described in detail in (4. Comparison of first and second embodiments) below, if the actuator 322 is arranged such that the rotational axis of the actuator 322 faces a direction substantially orthogonal to the direction in which the second arm unit 272 extends, the actuator 322 may protrude out toward the surgeon's body, and thus may impede the work of the surgeon. By arranging the actuator 322 such that the second axis $O_2$ and the rotational axis of the actuator 322 are substantially orthogonal to each other, as in the first embodiment, this kind of protruding portion can be substantially eliminated, so convenience for the surgeon is able to be further improved.

Also, although not illustrated, brakes that stop rotation of the joint units can be provided in the first joint unit 210 to the sixth joint unit 260. Note that the four rotating parts 245 to 248 of the fourth joint unit 240, i.e., the parallelogram link mechanism 240, rotate in conjunction with each other, so a brake is provided in at least one of these rotating parts 245 to 248. Note that the brake may be provide in each of the actuators 321 to 326 that correspond to the first joint unit 210 to the sixth joint unit 260.

The driving of these brakes is controlled by the control device 140. When a command to switch the operating mode of the support unit 120 to the locked mode is input via the operating mode toggle SW 153, these brakes are activated all at once under the control of the control device 140, and the corresponding rotational axes are consequently restrained. Also, when a command to switch the operating mode of the support unit 120 to the free mode is input via the operating mode toggle SW 153, these brakes are released all at once under the control of the control device 140.

Brakes which are released when energized and applied when de-energized, such as non-excitation-actuated electromagnetic brakes, for example, are preferably used for these brakes. Therefore, even in an emergency such as a power outage, the attitude of the support unit 120 is able to be maintained. Also, because there is no need to supply power in the locked mode in which the brakes are being applied, power consumption is able to be reduced. However, the first embodiment is not limited to this example. Any of various brake mechanisms used in a typical balance arm may be applied as these electronically controlled brake mechanisms. For example, these electronically controlled brake mechanisms may be electromagnetic brakes or mechanically driven brakes.

Figure 5:
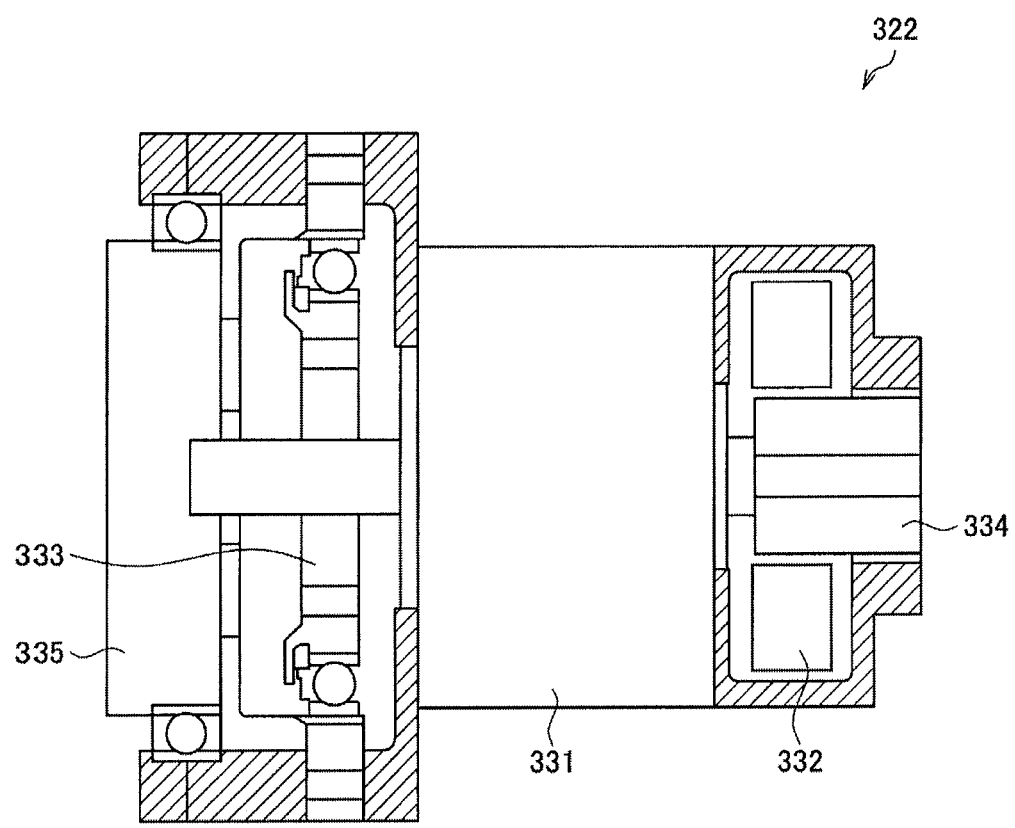
FIG. 5 is a sectional view illustrating a configuration example of an actuator illustrated in FIG. 4.

Here, in the first embodiment, actuators in which a servo mechanism in accordance with force control can be realized are used as the actuators 321 to 326. FIG. 5 is a sectional view illustrating a configuration example of the actuators 321 to 326 illustrated in FIG. 4. Note that all of the actuators 321 to 326 have a substantially similar configuration, so in FIG. 5, the configuration of the actuator 322 that rotatably drives the second joint unit 220 is illustrated as one example. Also, FIG. 5 illustrates a view of a cross section passing through the rotational axis of the actuator 322.

Referring to FIG. 5, the actuator 322 has a motor 331, a motor driver 332, a reducer 333, an encoder 334, and a torque sensor 335.

The motor 331 is a driving motor of the actuator 322, and generates rotary torque. Any of various motors typically used as a servo motor can be used as the motor 331. For example, the motor 331 is a brushless DC motor.

The motor driver 332 is a driver circuit (driver integrated circuit (driver IC)) that rotatably drives the motor 331 by supplying current to the motor 331. The motor driver 332 regulates the amount of current supplied to the motor 331 in accordance with the control amount of the second joint unit 220 calculated by the control device 140, and rotates the motor 331.

The reducer 333 is provided on a drive shaft (output shaft) on the output side of the motor 331, and generates a predetermined rotary torque by slowing the rotation of the output shaft generated by the motor 331 at a predetermined reduction ratio. For accurate positioning, a backlash-less high-performance reducer is preferably used as the reducer 333. Also, from the viewpoint of safety, a reducer having a relatively large reduction ratio of approximately 1/100, for example, is preferably used as the reducer 333 so that the rotation speed of the second joint unit 220 will not become too high. A Harmonic Drive (registered trademark) reducer, for example, as a reducer that can satisfy these requirements, can be used as the reducer 333. The rotary torque generated by the reducer 333 is transmitted to the second joint unit 220 via the power transmission mechanism described above, such that the second joint unit 220 rotates.

The encoder 334 is provided on a drive shaft (input shaft) on the input side of the motor 331, and detects the rotation speed of the input shaft. A detection value from the encoder 334 is transmitted to the control device 140, and used to ascertain the state of the support unit 120. More specifically, the control device 140 is able to obtain information such as the rotation angle, rotation angular velocity, and the rotation angular acceleration of the second joint unit 220, on the basis of the relationship among the rotation speed of the input shaft detected by the encoder 334, the reduction ratio of the reducer 333, and the gear ratio of the power transmission mechanism, and the like.

The torque sensor 335 is provided on the output shaft of the reducer 333, and detects torque generated by the reducer 333, i.e., rotary torque (generated torque) generated by the actuator 322. Also, the torque sensor 335 is able to detect not only the generated torque from the actuator 322, but also external torque applied externally. The detection value from the torque sensor 335 is transmitted to the control device 140, and used to ascertain the state of the support unit 120.

Note that the configuration example illustrated in FIG. 5 corresponds to force control. In a case where drive control of the second joint unit 220 is performed in accordance with position control, the torque sensor 335 does not necessarily have to be provided on the actuator 322.

(2-2. Structure of Power Transmission Mechanism)

Figure 6:
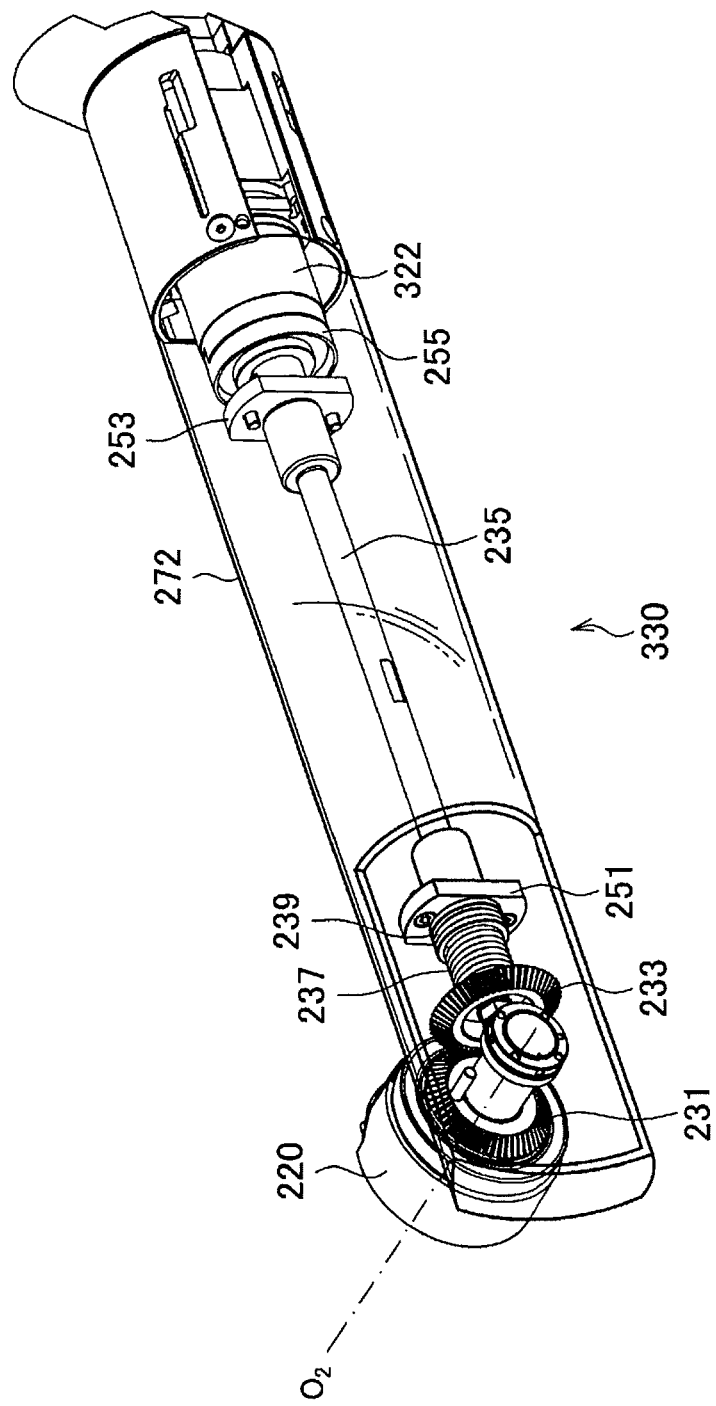
FIG. 6 is a view illustrating a configuration example of a power transmission mechanism that connects a second joint unit and an actuator, in the first embodiment.

The structure of the power transmission mechanism that connects the second joint unit 220 to the actuator 322 will be described in more detail with reference to FIG. 6. FIG. 6 is a view illustrating a configuration example of a power transmission mechanism that connects the second joint unit 220 to the actuator 322, in the first embodiment. In FIG. 6, only the structure near the second joint unit 220, the second arm unit 272, and the actuator 322, of the structure of the support unit 120 of the observation device 10 illustrated in FIG. 4, is extracted and illustrated. Also, in FIG. 6, a side wall of the second arm unit 272 is shown transparent, in a simulated manner, in order to illustrate the structure provided inside the second arm unit 272.

Referring to FIG. 6, the second joint unit 220 is arranged on the distal end side of the second arm unit 272, in a manner such that the second axis $O_2$ is substantially orthogonal to the direction in which the second arm unit 272 extends. Also, the actuator 322 is arranged on the proximal end side of the second arm unit 272, in a manner such that the rotational axis of the actuator 322 is substantially parallel to the direction in which the second arm unit 272 extends.

A power transmission mechanism 330 provided inside the second arm unit 272 includes a drive shaft 235 that extends along in a direction substantially parallel to the rotational axis of the actuator 322 (i.e., in the direction in which the second arm unit 272 extends), and is connected at one end to a rotating shaft of the actuator 322, and rotates on the same axis as the rotating shaft, a first bevel gear 233 that is provided on the other end of the drive shaft 235 and rotates on the same axis as the rotating shaft of the actuator 322, and a second bevel gear 231 that meshes with the first bevel gear 233 and rotates on the same axis as the second axis $O_2$ corresponding to the second arm unit 272. In this way, in the first embodiment, the rotation of the rotating shaft of the actuator 322 is transmitted to the second joint unit 220 by the first bevel gear 233 and the second bevel gear 231.

At this time, the rotation of the rotating shaft of the actuator 322 is transmitted to the first bevel gear 233 by the drive shaft 235 that extends along in the direction in which the second arm unit 272 extends, so the actuator 322 and the second joint unit 220 can be a predetermined distance apart. Therefore, the actuator 322 can be arranged away from the distal end region of the support unit 120, so the structure of the distal end region can be made smaller.

Also, rotation can be transmitted between two rotational axes that are orthogonal to each other by using the first bevel gear 233 and the second bevel gear 231. Therefore, according to the power transmission mechanism 330, the actuator 322 is able to be arranged such that the rotational axis of the actuator 322 is substantially parallel to the direction in which the second arm unit 272 extends. As a result, the amount that the actuator 322 protrudes in a direction substantially orthogonal to the direction in which the second arm unit 272 extends is able to be suppressed, so the protruding actuator 322 will not interfere with the surgeon's body. Consequently, a situation in which work by the surgeon is hindered from being performed smoothly can be avoided.

Furthermore, structures such as a backlash-less mechanism 237, a thrust bearing 239, linear guides 251 and 253, and an Oldham coupling 255 may be provided in the power transmission mechanism 330, as illustrated in the drawings.

The backlash-less mechanism 237 is provided on an end portion of the drive shaft 235, and is formed by a spring that urges the first bevel gear 233 in a direction that reduces the clearance between the first bevel gear 233 and the second bevel gear 231 (i.e., in a direction in which the first bevel gear 233 is pushed toward the second bevel gear 231). Because the clearance between the first bevel gear 233 and the second bevel gear 231 is reduced by the first bevel gear 233 being pushed toward the second bevel gear 231 by the spring, backlash in the meshing of the first bevel gear 233 and the second bevel gear 231 is suppressed.

In the electronic imaging observation device 10, there are cases where an image of the surgical site is captured at high magnification by the microscope unit 110, so if backlash were to occur in the driving of the support unit 120, it would be difficult to position the microscope unit 110 with high accuracy, and the desired portion may not be able to be smoothly observed. In the illustrated configuration example, the backlash-less mechanism 237 is provided in the power transmission mechanism 330, so the occurrence of backlash is able to be suppressed, and as a result, the position of the microscope unit 110 is able to be more accurately controlled.

However, because the backlash-less mechanism 237 is provided, the clearance between the first bevel gear 233 and the second bevel gear 231 is small, so when the first bevel gear 233 and the second bevel gear 231 rotate, the tooth faces are strongly pressed together, and force is loaded in the direction in which the drive shaft 235 extends, onto the first bevel gear 233 and the drive shaft 235 to which the first bevel gear 233 is connected. Therefore, in the illustrated configuration example, the linear guides 251 and 253 that guide movement in the direction in which the drive shaft 235 extends, are provided on the drive shaft 235.

Any of various well-known guides may be used as the linear guides 251 and 253. For example, the linear guides 251 and 253 are formed by a plate-shaped member having an opening through which the drive shaft 235 is inserted, and a bearing that enables the drive shaft 235 to slip in the direction in which the drive shaft 235 is inserted, and that is attached to this plate-shaped member at the inner periphery of the opening (i.e., at a portion in contact with the outer periphery of the drive shaft 235). Providing the linear guides 251 and 253 enables the movement of the drive shaft 235 in the direction in which the drive shaft 235 extends that accompanies the rotation of the first bevel gear 233 and the second bevel gear 231 to be smooth. As a result, the rotation of the first bevel gear 233 and the second bevel gear 231 is smooth, so the operation of the support unit 120 is smooth.

Thus, the positioning accuracy of the microscope unit 110 improves. Also, the operability when operating the support unit 120 improves.

Furthermore, the thrust bearing 239 may be provided on the drive shaft 235. The thrust bearing 239 suppresses friction loss that occurs when the drive shaft 235 rotates, which is due to the thrust load applied to the first bevel gear 233 and the drive shaft 235 as the first bevel gear 233 rotates. Consequently, the rotation of the first bevel gear 233 and the second bevel gear 231 is able to be smoother.

Also, the Oldham coupling 255 may be used to connect the rotating shaft of the actuator 322 to the drive shaft 235. Any of various well-known configurations can be used for the specific configuration of the Oldham coupling 255. Employing the Oldham coupling 255 makes the transmission of rotation between the rotating shaft of the actuator 322 and the drive shaft 235 smoother, i.e., enables the power from the actuator 322 to be more smoothly transmitted to the second joint unit 220.

Above, the structure of the observation system 1 and the observation device 10 according to the first embodiment has been described with reference to FIG. 4. Also, the structure of the power transmission mechanism 330 that connects the second joint unit 220 to the actuator 322 has been described with reference to FIG. 6.

As described above, in the first embodiment, the actuator 322 that applies driving force with respect to rotation about the second axis $O_2$ of the second joint unit 220 capable of defining the attitude of the microscope unit 110, and the second joint unit 220, are arranged separated from each other via the power transmission mechanism 330. The rotating shaft capable of defining the attitude of the microscope unit 110 is typically often provided near the microscope unit 110, so by arranging the actuator 322 and the second joint unit 220 apart from each other in this way, the structure near the microscope unit 110 is able to be made smaller. Therefore, when practicing medicine such as performing surgery or an examination using the observation device 10 according to the first embodiment, the workspace and field of view of the surgeon is able to be better ensured.

Also, in the first embodiment, the power transmission mechanism capable of transmitting rotation between two rotational axes that are substantially orthogonal to each other is used as the power transmission mechanism 330. Therefore, the actuator 322 can be arranged such that the second axis $O_2$ and the rotating shaft of the actuator 322 are orthogonal to each other, i.e., such that the rotating shaft of the actuator 322 points in a direction substantially parallel to the direction in which the second arm unit 272 extends. Accordingly, a situation in which the actuator 322 largely protrudes in a direction orthogonal to the direction in which the second arm unit 272 extends, and the protruding portion interferes with the surgeon, is able to be preferably prevented.

Here, typically as another structure of a power transmission mechanism that transmits rotation between two rotational axes, a structure in which a link or wire or the like is strung between rotating shafts and the rotation of one rotating shaft is transmitted to the other rotating shaft via linear movement in the direction in which the link or wire extends, is conceivable. However, in a power transmission mechanism that uses such a link or wire or the like, the transmissible rotation angle may be limited. Therefore, if a power transmission mechanism using a link or a wire or the like is applied to transmit rotary movement between the actuator 322 and the second joint unit 220 described above, the rotation angle of the second axis $O_2$ may be limited to a predetermined range. In order to be able to capture an image of an object to be observed from any direction, the range of motion of the microscope unit 110 needs to be as wide as possible, so it is undesirable that the rotation angle of the second axis $O_2$ be limited in this way.

On the other hand, with the power transmission mechanism 330 according to the first embodiment, the rotation of the drive shaft 235 that rotates in synchronization with the rotation of the rotating shaft of the actuator 322 is transmitted to the second joint unit 220 via the first bevel gear 233 and the second bevel gear 231. Therefore, because the transmissible rotation angle is not limited, the rotatable angular range of the second axis $O_2$ is able to be wider, so a wider range of motion of the microscope unit 110 is able to be ensured.

Note that in the embodiment described above, the power transmission mechanism 330 is provided between the second joint unit 220, and the actuator 322 that applies driving force with respect to rotation about the second axis $O_2$ that is the rotational axis of the second joint unit 220, but the first embodiment is not limited to this example. Among the joint units provided in the support unit 120, the joint unit to be arranged separated from the actuator with the power transmission mechanism 330 interposed between the joint unit and the actuator is not limited to the second joint unit 220, and may be another joint unit as long as the joint unit is able to define the attitude of the microscope unit 110 and be arranged near the microscope unit 110. For example, the power transmission mechanism 330 may be provided between the third joint unit 230, and the actuator 323 that applies driving force with respect to rotation about the third axis $O_3$ that is the rotational axis of the third joint unit 230, and the third joint unit 230 and the actuator 323 may be arranged separated from each other.

Alternatively, a configuration may be provided in which an actuator is separated from a plurality of joint units, such as the second joint unit 220 and the third joint unit 230, for example, via the power transmission mechanism 330. By employing a configuration in which, for at least one joint unit capable of defining the attitude of the microscope unit 110, the joint unit and the actuator are arranged separated from each other via the power transmission mechanism 330, the structure near the microscope unit 110 is able to be made smaller.

Also, in the embodiment described above, the first bevel gear 233 and the second bevel gear 231 are used as the power transmission mechanism 330. However, the first embodiment is not limited to this example. The power transmission mechanism 330 need only be configured to be able to transmit rotation between rotating shafts that are orthogonal to each other. Other mechanical elements may also be used as the specific structure. For example, the power transmission mechanism 330 may be formed by a worm gear. The worm gear can be formed by a worm that is connected at one end to the rotating shaft of the actuator 322 and rotates on the same axis as the rotating shaft of the actuator 322, and a worm wheel that is in mesh with the tooth face of the worm and rotates on the same axis as the second axis $O_2$.

(2-3. Modified Example of Actuator)

The actuator 322 described with reference to FIG. 5 responds to so-called relatively advanced control, and is able to realize a servo mechanism. However, the actuator 322 configured to be able to respond to this kind of advanced control is relatively expensive, and has a tendency to become large, particularly in the radial direction (the in-plane direction perpendicular to the drive shaft). As described with reference to FIG. 6, the drive shaft (rotating shaft) of the actuator 322 is arranged inside the second arm unit 272 so as to point in a direction substantially parallel to the direction in which the second arm unit 272 extends. Therefore, if the outer diameter of the actuator 322 becomes larger, the outer diameter of the second arm unit 272 will also become larger. As a result, the structure near the microscope unit 110 may not be able to be effectively made smaller.

On the other hand, if only simpler control need be performed, the size of the actuator 322, particularly the size in the radial direction, can be made smaller. Therefore, if only simple control is performed at the second joint unit 220 and/or the third joint unit 230 that need to be made smaller, the actuators 322 and 323 provided in these joint units can be made smaller. Here, one configuration example of smaller actuators 322a and 323a will be described as a modified example of the actuators 322 and 323.

Figure 7:
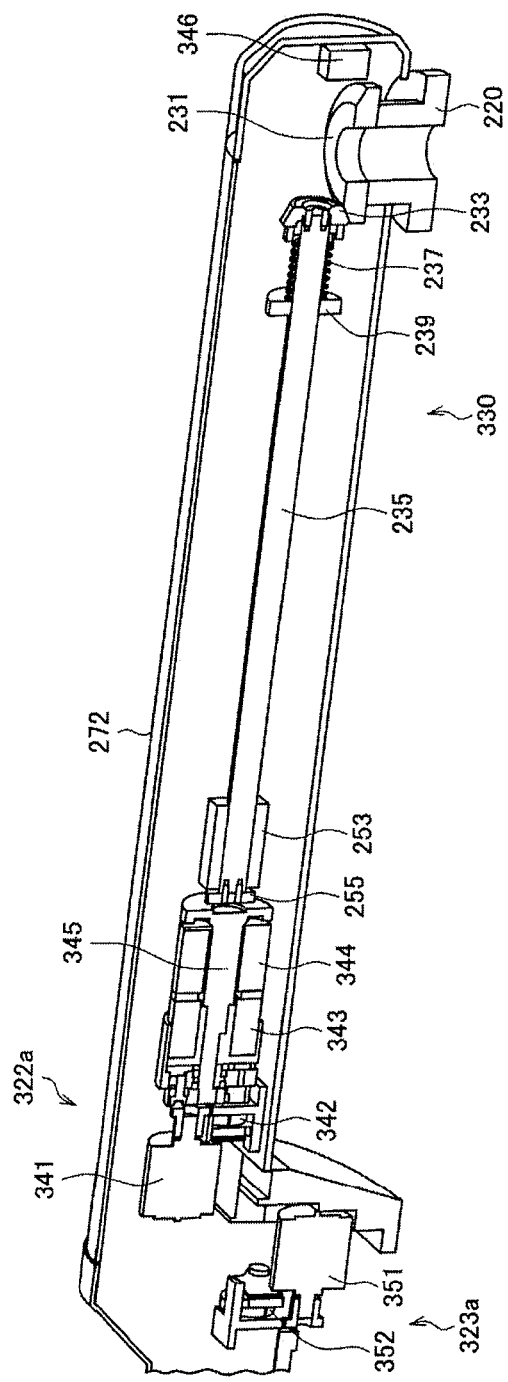
FIG. 7 is a sectional view illustrating a configuration example of an actuator according to a modified example of the first embodiment.
Figure 8:
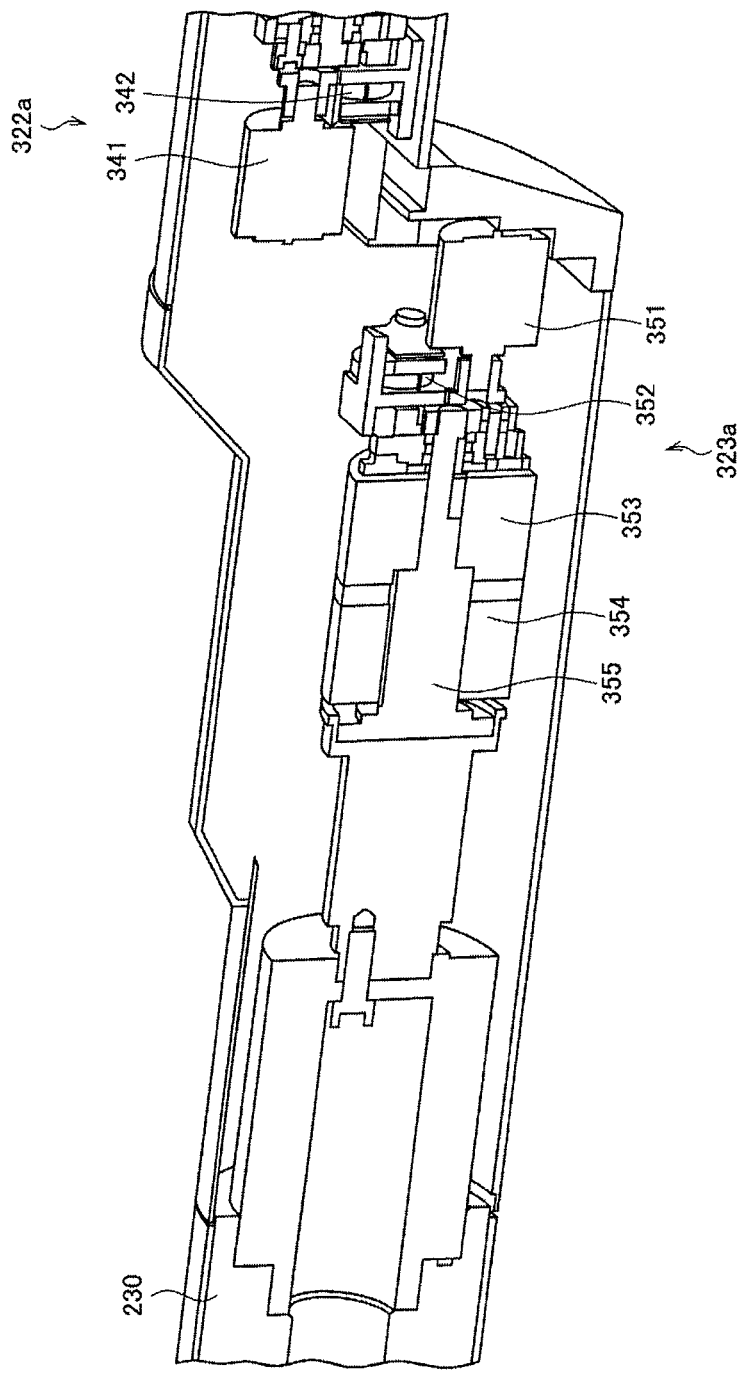
FIG. 8 is a sectional view illustrating a configuration example of an actuator according to a modified example of the first embodiment.

FIG. 7 and FIG. 8 are sectional views illustrating a configuration example of the actuators 322a and 323a according to a modified example of the first embodiment. FIG. 7 illustrates the second arm unit 272 and the structure near the second arm unit 272 in a state cut along a cross section passing through in the direction in which the second arm unit 272 extends and the rotational axis direction of the second joint unit 220. FIG. 8 illustrates the third arm unit 273 and the structure near the third arm unit 273 in a state cut along a cross section passing through in the direction in which the third arm unit 273 extends and the rotational axis direction of the third joint unit 230.

Note that in the present modified example, the actuators 322 and 323 in the structure according to the embodiment described above have been replaced with the actuators 322a and 323a, and the other structure, such as the power transmission mechanism 330, is substantially similar to the structure of the embodiment described above. Therefore, in the description of the present modified example below, mainly the structure of the actuators 322a and 323a that differs from the embodiment described above will be described. A detailed description of the other structure will be omitted. Note that in FIG. 7, some of the members illustrated in FIG. 6 are omitted for simplicity.

Here, in the present modified example, the actuators 322a and 323a are configured such that at least an xy movement operation can be executed in the second joint unit 220 and the third joint unit 230. Therefore, the configuration example of the actuators 322a and 323a illustrated in FIG. 7 and FIG. 8 also corresponds to an xy movement operation. Here, an xy movement operation is an operation in which the control device 140 moves the microscope unit 110 by driving the second joint unit 220 and the third joint unit 230 such that the display on the display device 20 moves parallel to the left-and-right direction or the up-and-down direction, in accordance with an operation dictating the direction by the surgeon via an input device such as arrow keys or a lever, for example.

For example, the relatively large and expensive actuators 322 and 323 corresponding to a servo mechanism, such as the actuators illustrated in FIG. 5 described above, are necessary to perform an operation requiring advanced control such as a pivot operation (an operation that moves the microscope unit 110 such that the optical axis of the microscope unit 110 always points to a predetermined point in space), for example. On the other hand, an xy movement operation is able to be realized by the less expensive, smaller actuators 322a and 323a. Also, depending on the type of surgery or the like, there are often cases in which as long as an xy movement operation is able to be executed, that xy movement operation is practically sufficient, and an operation requiring advanced control such as a pivot operation does not have to be performed. Therefore, the present modified example illustrates a configuration example of the actuators 322a and 323a capable of realizing at least an xy movement operation, as one example of a less expensive, smaller actuator.

First, the configuration of the actuator 322a provided in the second joint unit 220 will be described. Referring to FIG. 7, the actuator 322a according to the present modified example is configured with a motor 341, a reduction mechanism 342, a clutch 343, and a brake 344 connected in series (i.e., lined up in one direction) in this order. Note that as described above, in the first embodiment, a brake can be provided for the second joint unit 220, but in the case where the actuator 322a according to the present modified example is used, the actuator 322a itself is equipped with the brake 344, so there is no need to provide a separate brake for the second joint unit 220.

The rotation of the output shaft of the motor 341 is appropriately slowed by the reduction mechanism 342 and transmitted to a drive shaft 345 via the clutch 343. One end of the drive shaft 235 of the power transmission mechanism 330 is connected to the distal end of the drive shaft 345 via the Oldham coupling 255. The rotation of the drive shaft 345 is transmitted to the second joint unit 220 via the drive shaft 235, the first bevel gear 233, and the second bevel gear 231. Moreover, the brake 344 is provided on the drive shaft 345, and the rotation and arrest of the second joint unit 220 are respectively controlled by the brake 344 releasing and restraining the drive shaft 345.

A stepping motor, for example, is used as the motor 341. A stepping motor is less expensive than the brushless DC motor used in the actuator 322 described above, although the resolution of the rotation angle is lower. The resolution of the rotation angle does not need to be that accurate to perform an xy movement operation, so a less expensive stepping motor can be preferably used as the motor 341. Note that in the present modified example, the motor 341 is preferably configured such that the size of the motor 341 in the radial direction (the area in a plane perpendicular to the direction in which the drive shaft 345 extends) is smaller than the size of the clutch 343 or the brake 344 in the radial direction. The reason for this will be described later.

An electromagnetic clutch capable of electrically controlling the transmission and interruption of rotation is used as the clutch 343. For example, the clutch 343 is a so-called excitation-actuated clutch that transmits rotation when energized. The operation of the clutch 343 is controlled by the control device 140. Note that the type of the clutch 343 is not limited. Any of a variety of well-known electromagnetic clutches can be used. However, using an excitation-actuated clutch as in the embodiment enables the safety of surgery and the examinations to be further increased. For example, in the unlikely event that power is lost for some reason, if the motor 341 is connected to a downstream member by the clutch 343, rotation of the second joint unit 220 will be locked, and the support unit 120 will be unable to be moved manually, which may make it difficult to continue surgery or an examination. On the other hand, if an excitation-actuated clutch is used, the motor 341 will be disconnected from the downstream members at the time power is lost, so the support unit 120 can be moved manually, thus making it possible to continue the surgery or examination, so greater safety can be realized.

An electromagnetic brake capable of electrically controlling the release and restraint of the drive shaft 345 is used as the brake 344. For example, the brake 344 is a so-called non-excitation-actuated brake that restrains the drive shaft 345 when de-energized. The operation of the brake 344 is controlled by the control device 140. Note that the type of the brake 344 is not limited. Any of a variety of well-known electromagnetic brakes can be used. However, using a non-excitation-actuated brake as in the first embodiment makes it possible to increase the safety of surgery and examinations because even in the unlikely event that power is lost for some reason, for example, the brake 344 will be applied and rotation of the second joint unit 220 will be stopped. Also, because during surgery or an examination the time during which the attitude of the support unit 120 is fixed (i.e., the time during which the brake 344 and the brake of another joint unit are applied) is much longer than the time during which the support unit 120 is moving, using a non-excitation-actuated brake makes it possible to reduce power consumption as well as increase the life of the brake 344.

The reduction mechanism 342 is formed by a plurality of gears, and slows the rotation of the output shaft of the motor 341 at a predetermined reduction ratio. Here, the reduction mechanism 342 need only be configured to have a predetermined reduction ratio capable of realizing the rotation torque ultimately desired to be obtained. The specific configuration of the reduction mechanism 342 is not limited. However, in the present modified example, the reduction mechanism 342 is preferably configured such that the size of the reduction mechanism 342 in the radial direction (the area in a plane perpendicular to the direction in which the drive shaft 345 extends) is smaller than the size of the clutch 343 or the brake 344 in the radial direction, similar to the motor 341.

The reason for configuring the motor 341 and the reduction mechanism 342 in this way is because in a case where the actuator 322a is actually designed using a stepping motor is used as the motor 341, using an excitation-actuated clutch as the clutch 343, and using a non-excitation-actuated brake as the brake 344 as described above, the outer diameter of the actuator 322a depends on the outer diameter of the clutch 343 or the brake 344. That is, the outer diameter of the actuator 322a can be minimized by configuring the motor 341 and the reduction mechanism 342 such that the size of the motor 341 and the reduction mechanism 342 in the radial direction is smaller than the size of the clutch 343 or the brake 344 in the radial direction. As illustrated in FIG. 7, the actuator 322a is provided inside the second arm unit 272, such that the drive shaft 345 of the actuator 322a is substantially parallel to the direction in which the second arm unit 272 extends. Therefore, if the outer diameter of the actuator 322a can be minimized, the outer diameter of the second arm unit 272 can be minimized. That is, the second arm unit 272 can be made even smaller.

Here, similar to the reducer 333 of the actuator 322 illustrated in FIG. 5 described above, a relatively large reduction ratio such as 1/100, for example, is needed in the reduction mechanism 342 as well in order to realize even slower rotation of the second joint unit 220. That is, the reduction mechanism 342 needs to have a large reduction ratio while being small in the radial direction. Study by the inventors revealed that this can be realized by having all of the gears that form the reduction mechanism 342 be spur gears. That is, forming the reduction mechanism 342 with only spur gears makes it possible to realize the reduction mechanism 342 that is smaller and has a relatively large reduction ratio.

Note that if the reduction mechanism 342 is formed using gears other than spur gears, such as a worm gear, for example, a large reduction ratio can be realized by a simpler configuration due to there being fewer gears. However, study by the inventors revealed that it is extremely difficult to make the size of the reduction mechanism 342 in the radial direction smaller than the size of the clutch 343 or the brake 344 in the radial direction in a case where a configuration in which rotating shafts of gears are orthogonal to each other, as they are with a worm gear, is included. Therefore, in order to minimize the reduction mechanism 342, the reduction mechanism 342 is preferably configured such that all of the rotational axes of the plurality of gears that form the reduction mechanism 342 are substantially parallel, as they are with the configuration described above in which the reduction mechanism 342 is formed with only spur gears.

Heretofore, the configuration of the actuator 322a provided in the second joint unit 220 has been described. Note that in a case where the actuator 322a is configured as in the present modified example, the length in the direction in which the drive shaft 345 extends can be longer, while the size in the radial direction can be smaller, compared to the actuator 322 in the embodiment described above. However, as illustrated in FIG. 7, the actuator 322a is provided inside the second arm unit 272, such that the drive shaft 345 of the actuator 322a is substantially parallel to the direction in which the second arm unit 272 extends. The second arm unit 272 is originally a long member because of the nature of the "arm", so even if the actuator 322a is arranged inside the second arm unit 272 such that the drive shaft 345 is substantially parallel to the direction in which the second arm unit 272 extends, it will not affect the size (length) in the direction in which the second arm unit 272 itself extends. In this way, the configuration of the actuator 322a having the characteristic in which the length in the direction in which the drive shaft 345 extends may be longer but the size in the radial direction can be made smaller, preferably fits the configuration according to the first embodiment in which the actuator 322a and the second joint unit 220 are separated from each other and the rotational axes of the actuator 322a and the second joint unit 220 are arranged orthogonal to each other.

Next, the configuration of the actuator 322a provided in the third joint unit 230 will be described. Note that the configuration of the actuator 323a is substantially similar to the configuration of the actuator 322a described above. More specifically, referring to FIG. 8, the actuator 323a according to the present modified example is configured with a motor 351, a reduction mechanism 352, a clutch 353, and a brake 354 connected in series (i.e., lined up in one direction) in this order. Note that similar to the second joint unit 220, in the case where the actuator 323a according to the present modified example is used, the actuator 323a itself is equipped with the brake 354, so there is no need to provide a separate brake for the third joint unit 230.

The rotation of the output shaft of the motor 351 is appropriately slowed by the reduction mechanism 352 and transmitted to a drive shaft 355 via the clutch 353. The rotation of the drive shaft 355 is transmitted to the third joint unit 230 via a transmitting member. The brake 354 is provided on the drive shaft 355, and the rotation and arrest of the third joint unit 230 are respectively controlled by the brake 354 releasing and restraining the drive shaft 355.

The configurations of the motor 351, the reduction mechanism 352, the clutch 353, and the brake 354 are similar to the configurations of the motor 341, the reduction mechanism 342, the clutch 343, and the brake 344 of the actuator 322a, so detailed descriptions of these will be omitted. Similar to the actuator 322a, the actuator 322a can be configured such that the outer diameter is as small as possible, so the outer diameter of the third arm unit 273 can be minimized, i.e., the third arm unit 273 can be smaller. By applying the actuator 322a as the actuator provided in the second joint unit 220 and applying the actuator 323a as the actuator provided in the third joint unit 230 in this way, the second arm unit 272 and the third arm unit 273 can be made smaller, so the structure near the microscope unit 110 can be even smaller, compared to the embodiment described above.

Here, in the illustrated configuration example, an encoder is not provided on the actuators 322a and 323a, which differs from the actuator 322 according to the embodiment described above. However, in order to perform the xy movement operation, it is necessary to detect the rotational angle of the second joint unit 220 and the third joint unit 230. Therefore, in the present modified example, a potentiometer 346 for detecting the rotation angle of the second joint unit 220 is provided near the second joint unit 220, instead of providing an encoder on the actuator 322a. Also, although not illustrated, for the third joint unit 230 as well, a potentiometer for detecting the rotation angle of the third joint unit 230 is provided near the third joint unit 230, instead of providing an encoder on the actuator 323a.

The detection values from these potentiometers are transmitted to the control device 140. The control device 140 is able to ascertain the state of the support unit 120 and calculate the control amounts of the joint units 210 to 260 in order to realize xy movement in response to an operation by the surgeon, on the basis of these detection values and the detection values from the encoders of the actuators 321, 324, 325, and 326 of the other joint units. Then, the xy movement operation can be realized by the control device 140 driving the actuators 321, 322a, 323a, 324, 325, and 326 of the joint units 210 to 260 in accordance with these control amounts.

In the present modified example, the operating mode of the support unit 120 is switched among a locked mode, an all free mode, and an xy movement operating mode for performing an xy movement operation, by operation of the actuators 322a and 323a described above, as well as the actuators 321, 324, 325, and 326 and brakes provided on the other joint units 210 and 240 to 260. Note that switching among these operating modes is accomplished by the surgeon inputting a command via the operating mode toggle SW described above or another suitable input device.

Here, control of the actuators 322a and 323a in each of the locked mode, the all free mode, and the xy movement operating mode will be described. The control device 140 switches the driving of the motors 341 and 351, the clutches 343 and 353, and the brakes 344 and 354 of the actuators 322a and 323a, as illustrated in Table 1 below, in accordance with each mode. Note that in Table 1 below, the clutches 343 and 353 are assumed to be excitation-actuated clutches, so "ON" indicates a state in which rotation is being transmitted, and the brakes 344 and 354 are assumed to be non-excitation-actuated brakes, so "ON" indicates a state in which the drive shafts 345 and 355 are released.

TABLE 1

|  | Locked mode | All free mode | xy movement operating mode |
|---|---|---|---|
| Motors | OFF | OFF | ON |
| Clutches | OFF | OFF | ON |
| Brakes | OFF | ON | ON |

As illustrated in Table 1 above, in the present modified example, in the locked mode and the all free mode, the clutches 343 and 353 are released and the second joint unit 220 and the third joint unit 230 are not connected to the actuators 322a and 323a, respectively. Therefore, the second joint unit 220 and the third joint unit 230 are separated from the motors 341 and 351 and the reduction mechanisms 342 and 352, respectively, so in the all free mode, the second joint unit 220 and the third joint unit 230 will not be affected by detent torque of the motors 341 and 351 and can thus be moved more lightly. Also, in the locked mode, the clutches 343 and 353 and the brakes 344 and 354 are not energized, and in the all free mode, the clutches 343 and 353 are not energized, so power consumption in these modes can be reduced.

Only in the xy movement operation mode are the second joint unit 220 and the third joint unit 230 connected to the actuators 322a and 323a by the clutches 343 and 353, the second joint unit 220 and the third joint unit 230 driven by the actuators 322a and 323a. Note that more specifically, when the mode is switched from the locked mode or the all free mode to the xy movement operation mode, the motors 341 and 351 start to rotate after the motors 341 and 351 are energized, the clutches 343 and 353 are connected, and the brakes 344 and 354 are released, in this order. Conversely, when the mode is switched from the xy movement operation mode to the locked mode or the all free mode, excitation of the motors 341 and 351 stops after the motors 341 and 351 stop rotating, the drive shafts 345 and 355 are restrained by the brakes 344 and 354, and the clutches 343 and 353 are released, in this order. The shift among modes is able to be performed more safely by shifting among modes in such a sequence.

3. Second Embodiment

A second embodiment of the present disclosure will now be described. In the second embodiment as well, an observation device in which the structure of the distal end region is smaller can be realized by arranging the second joint unit away from the actuator that applies driving force with respect to rotation about the second axis $O_2$ that is the rotational axis of the second joint unit, similar to the first embodiment. However, in the second embodiment, the structure of the power transmission mechanism that transmits the driving force of the actuator to the second joint unit differs from the structure in the first embodiment. In the second embodiment, the structure other than the structure of the power transmission mechanism may be similar to the structure in the first embodiment, so in the description of the second embodiment below, mainly those matters that differ from the first embodiment will be described. A detailed description of matter similar to matter of the first embodiment will be omitted.

(3-1. Structure of Observation System and Observation Device)

Figure 9:
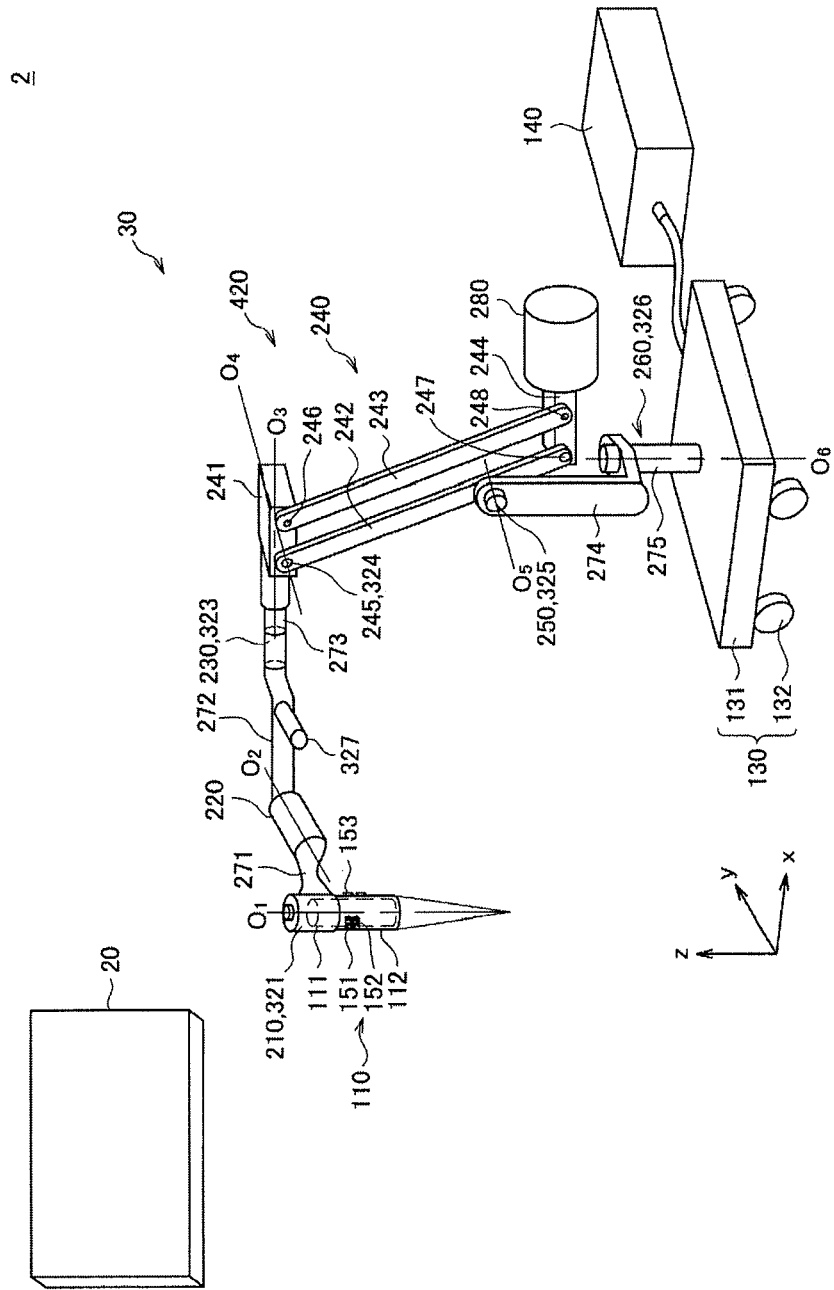
FIG. 9 is a view illustrating a configuration example of an observation system according to a second embodiment.

The structure of an observation system according to the second embodiment of the present disclosure, and the structure of an observation device that forms the observation system, will be described with reference to FIG. 9. FIG. 9 is a view illustrating a configuration example of the observation system according to the second embodiment.

Referring to FIG. 9, the observation system 2 according to the second embodiment includes an observation device 30 that supports a microscope unit 110 and captures an image of a surgical site of a patient with the microscope unit 110, and a display device 20 that displays an image of the surgical site captured by the observation device 30. Note that the structure and function of the display device 20 are similar to the structure and function in the first embodiment, so a detailed description of the structure and function will be omitted here.

The observation device 30 includes the microscope unit 110 for performing magnified observation of a surgical site of the patient, a support unit 420 (arm unit 420) that supports the microscope unit 110, a base unit 130 to which one end of the support unit 420 is connected and which supports the microscope unit 110 and the support unit 420, and the control device 140 that controls the operation of the observation device 30. Here, the structure and function of the microscope unit 110, the base unit 130, and the control device 140 are similar to the structure and function in the first embodiment, so a detailed description of the structure and function will be omitted here.

The structure of the support unit 420 is also substantially similar to the structure of the support unit 120 according to the first embodiment. However, in the support unit 420, the structure of the power transmission mechanism that transmits the driving force of the actuator to the second joint unit 220 differs from the structure in the first embodiment, as described above. Accordingly, in the support unit 420, an actuator 327 is provided instead of the actuator 322 provided for the second joint unit 220 in the support unit 120.

When describing the arrangement of the actuator 327 in detail, in the second embodiment as well, the actuator 327 is provided in a position separated from the second joint unit 220, similar to the first embodiment. More specifically, the actuator 327 is provided on the proximal end portion of the second arm unit 272, and is connected to the second joint unit 220 provided on the distal end portion of the second arm unit 272, by a power transmission mechanism (not illustrated) provided inside the second arm unit 272. In this way, in the second embodiment, the second joint unit 220 and the actuator 327 that applies driving force with respect to rotation about the second axis $O_2$ that is the rotational axis of the second joint unit 220 are arranged separated from each other via the power transmission mechanism, similar to the first embodiment. Accordingly, the actuator 327 is able to be arranged in a position away from the second joint unit 220, so the second joint unit 220, i.e., the structure of the distal end region, is able to be smaller.

However, in the second embodiment, a power transmission mechanism capable of transmitting rotation between two rotational axes that are substantially parallel to each other, which is different from the first embodiment, is used as the power transmission mechanism that connects the second joint unit 220 and the actuator 327. Accordingly, the actuator 327 is arranged such that the second axis $O_2$ and the rotational axis of the actuator 327 are substantially parallel. That is, in the first embodiment, the actuator 322 is arranged such that the direction of the rotational axis of the actuator 322 is parallel to the direction in which the second arm unit 272 extends, but in the second embodiment, the actuator 327 is arranged such that the direction of the rotational axis of the actuator 327 is substantially orthogonal to the direction in which the second arm unit 272 extends, as illustrated in the drawing, due to the difference in the structure of the power transmission mechanism.

Note that although the arrangement is different, the structure itself of the actuator 327 may be similar to the structure of the actuator 323. That is, the actuator 327 has the structure illustrated in FIG. 5, for example.

(3-2. Structure of Power Transmission Mechanism)

Figure 10:
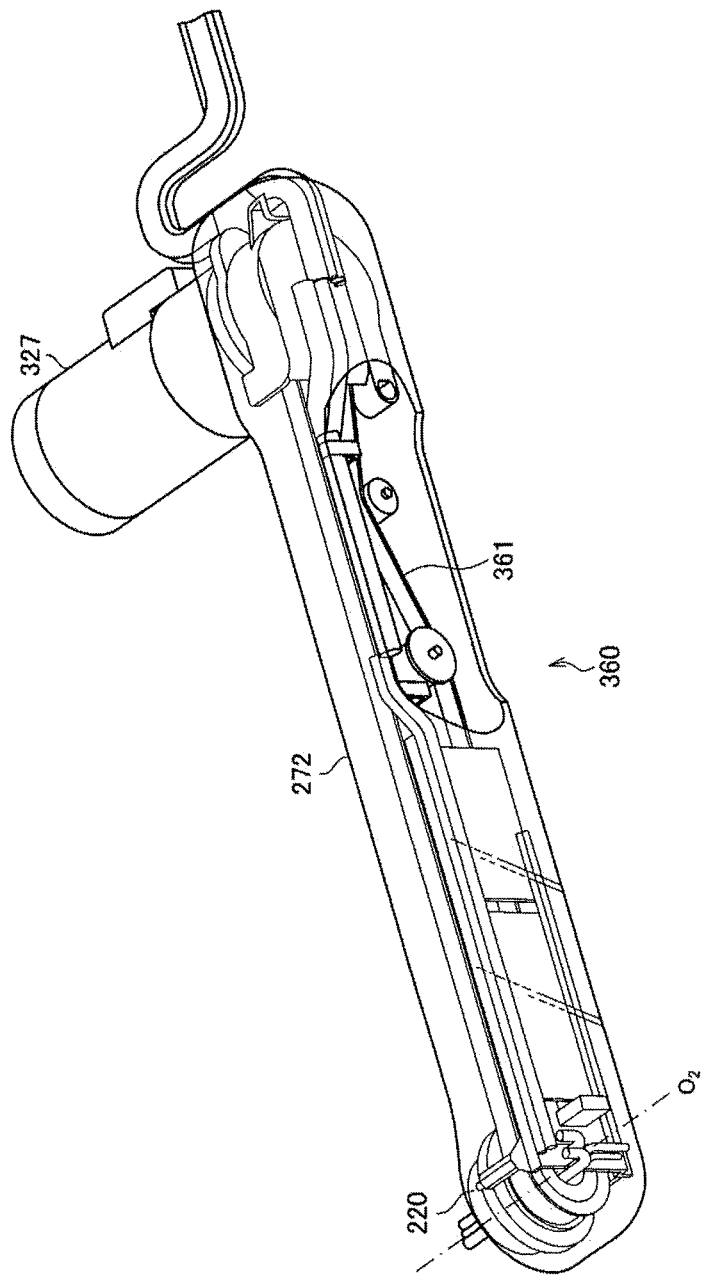
FIG. 10 is a view illustrating a configuration example of a power transmission mechanism that connects a second joint unit and an actuator, in the second embodiment.
Figure 11:
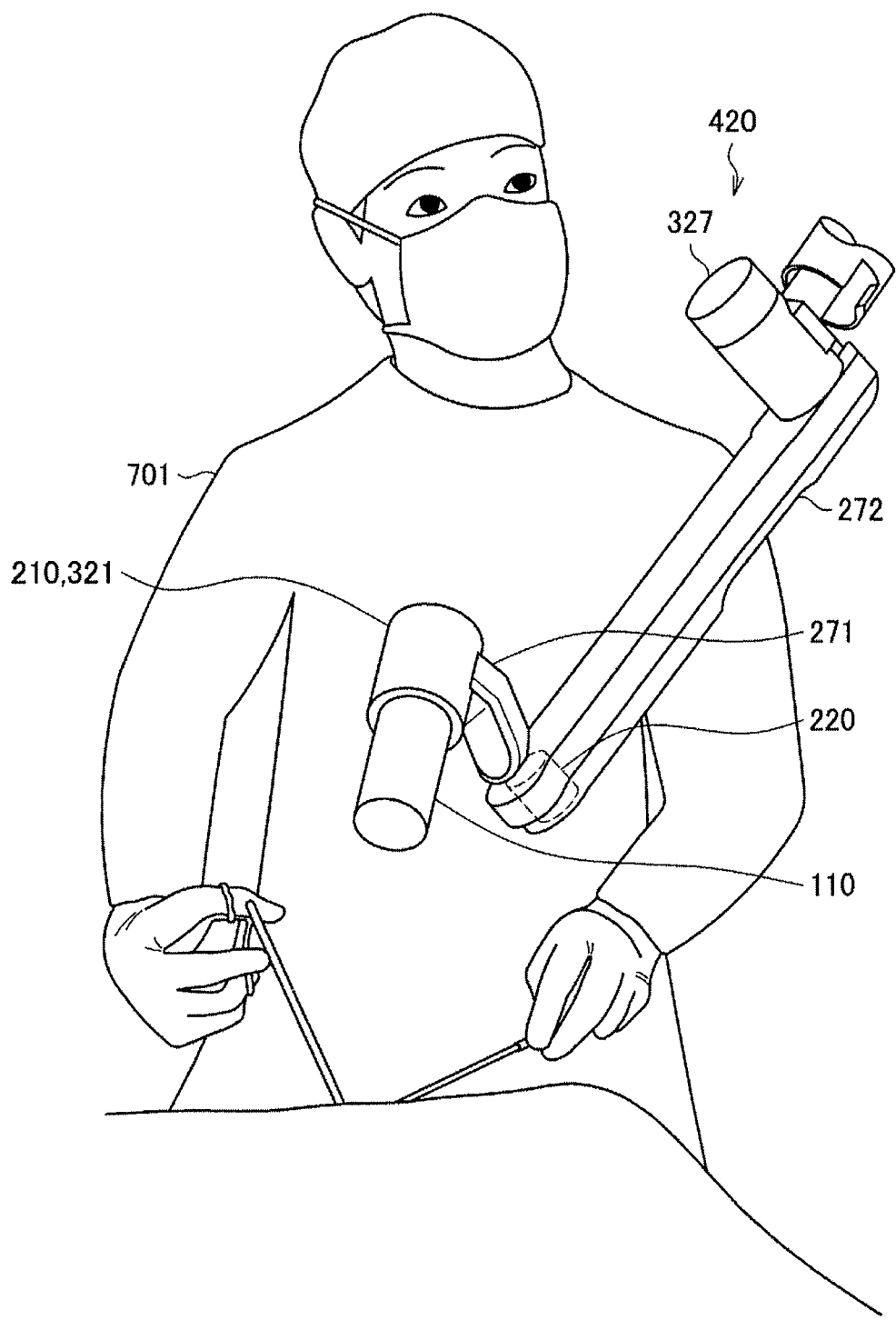
FIG. 11 is a schematic view illustrating the positional relationship between a support unit and an operator during surgery using the observation device according to the second embodiment.

The structure of the power transmission mechanism that connects the second joint unit 220 to the actuator 327 will be described in more detail with reference to FIG. 10. FIG. 10 is a view illustrating a configuration example of the power transmission mechanism that connects the second joint unit 220 to the actuator 327, in the second embodiment. In FIG. 10, only the structure near the second joint unit 220, the second arm unit 272, and the actuator 327, of the structure of the support unit 420 illustrated in FIG. 10 and FIG. 11, is extracted and illustrated. Also, in FIG. 10, a side wall of the second arm unit 272 is shown transparent, in a simulated manner, in order to illustrate the structure provided inside the second arm unit 272. Also, a portion of the side wall of the second arm unit 272 is shown open, in a simulated manner, for illustrative purposes.

Referring to FIG. 10, a power transmission mechanism 360 provided inside the second arm unit 272 includes a belt 361 that extends along in the direction in which the second arm unit 272 extends, and is wound between a rotating shaft of the actuator 327 and a drive shaft of the second joint unit 220 (i.e., a drive shaft corresponding to the second axis $O_2$). In this way, in the second embodiment, the rotation of the rotating shaft of the actuator 327 is transmitted to the second joint unit 220 by the belt 361.

The rotation of the rotating shaft of the actuator 327 is transmitted to the second joint unit 220 by the belt 361 that extends along in the direction in which the second arm unit 272 extends, so there is able to be a predetermined distance between the actuator 327 and the second joint unit 220. Therefore, the actuator 327 can be arranged away from the distal end region of the support unit 420, so the structure of the distal end region can be made smaller.

Above, the structure of the power transmission mechanism 360 that connects the second joint unit 220 to the actuator 327 has been described with reference to FIG. 10. Note that the actuators provided for the joint units 210 to 260 in the second embodiment may have a structure similar to the structure of the actuator 322 described with reference to FIG. 5, or may have a structure similar to the structure of the actuators 322a and 323a described in (2-3. Modified example of actuator) above. In FIG. 10, a configuration example of a case where the actuator 327 having a structure similar to the structure of the actuator 322 illustrated in FIG. 5 is illustrated as an example.

As described above, in the second embodiment, the actuator 327 that applies driving force with respect to rotation about the second axis $O_2$ that is the rotational axis of the second joint unit 220 capable of defining the attitude of the microscope unit 110, and the second joint unit 220, are arranged separated from each other via the power transmission mechanism 360. Therefore, similar to the first embodiment, the structure near the microscope unit 110 can be made smaller so the workspace and field of view of the surgeon is able to be better ensured when practicing medicine such as performing surgery or an examination using the observation device 30 according to the second embodiment.

Note that in the second embodiment, the rotation of the rotating shaft of the actuator 327 is directly transmitted to the second joint unit 220 by the belt 361, so the rotatable angular range of the second axis $O_2$ is able to be wider than it can a case in which a power transmission mechanism that uses a link or a wire or the like is used, as in the first embodiment. Therefore, the range of motion of the microscope unit 110 is able to be wider.

Also, in the second embodiment as well, similar to the first embodiment, among the joint units 210 to 260 provided in the support unit 420, the joint unit that is to be arranged separated from the actuator with the power transmission mechanism 360 interposed between the joint unit and the actuator is not limited to the second joint unit 220, and may be another joint unit as long as the joint unit is able to define the attitude of the microscope unit 110. Also, the specific configuration of the power transmission mechanism 360 is not limited to using the belt 361 described above. The power transmission mechanism 360 need only be configured to be able to transmit rotation between rotational axes that are substantially parallel to each other. Other mechanical elements may also be used as the specific structure.

4. Comparison of First and Second Embodiments

As described above, in the first and second embodiments, the second joint unit 220 and the actuators 322 and 327 are able to be arranged separated from each other by interposing the power transmission mechanisms 330 and 360 in between, which enables the structure of the distal end region to be made smaller. However, in the first and second embodiments, the configurations of the power transmission mechanisms 330 and 360 are different, so the arrangements of the actuators 322 and 327 in the second arm unit 272 are different.

More specifically, the power transmission mechanism 330 according to the first embodiment is configured to be able to transmit rotation between two rotational axes that are substantially orthogonal to each other. Therefore, the actuator 322 can be arranged with respect to the second arm unit 272 such that the direction in which the second arm unit 272 extends and the rotational axis direction of the actuator 322 are substantially parallel. As a result, the actuator 322 and the second arm unit 272 can be arranged such that the amount that the actuator 322 protrudes from the second arm unit 272 is less.

On the other hand, the power transmission mechanism 360 according to the second embodiment is configured to be able to transmit rotation between two rotational axes that are substantially parallel to each other. Therefore, the actuator 327 can be arranged with respect to the second arm unit 272, such that the direction in which the second arm unit 272 extends and the rotational axis direction of the actuator 327 are substantially orthogonal. Consequently, there is a possibility that the actuator 327 will largely protrude from the second arm unit 272 in a direction orthogonal to the direction in which the second arm unit 272 extends. Such a protruding portion may impede an operation by surgeon when performing surgery or an examination using the observation device 30 according to the second embodiment.

A state of surgery using the observation device 30 according to the second embodiment is schematically illustrated in FIG. 11. FIG. 11 is a schematic view illustrating the positional relationship between the support unit 420 and the surgeon during surgery using the observation device 30 according to the second embodiment. In FIG. 11, the positional relationship between the structure on the distal end side of the second arm unit 272 of the support unit 420 of the observation device 30, and a surgeon 701 performing surgery while referring to an image of the surgical site captured by the microscope unit 110 of the observation device 10, is schematically shown.

As illustrated in the drawing, when performing surgery using the observation device 30, the second arm unit 272 and the actuator 327 can be positioned near the body (the face in the illustrated example) of the surgeon. During surgery, the support unit 420 of the observation device must be kept so-called clean, but the body of the surgeon 701 belongs to an unclean area, so it is not permissible for the support unit 420 and the body of the surgeon 701 to come into contact with each other. However, in the second embodiment, the actuator 327 can largely protrude in the direction orthogonal to the direction in which the second arm unit 272 extends, so the risk of contact between the actuator 327 and the body of the surgeon 701 increases. Also, the surgeon 701 must work while avoiding the actuator 327 so that his or her body does not come into contact with the actuator 327 when he or she moves for work, for example. Consequently, the surgeon 701 may not be able to perform work smoothly.

On the other hand, in the first embodiment, the actuator 322 and the second arm unit 272 can be arranged such that the amount that the actuator 322 protrudes from the second arm unit 272 is less. Therefore, the risk of contact between the body of the surgeon 701 and the support unit 120 is able to be reduced. In this way, from the viewpoint of reliably ensuring the clean area, the power transmission mechanism 330 that is capable of transmitting rotation between two rotational axes that are substantially orthogonal to each other is preferably used, as in the first embodiment.

However, while the power transmission mechanism 360 according to the second embodiment is realized by the relatively simple structure of the belt 361, in the case where power is transmitted using bevel gears like the power transmission mechanism 330 according to the first embodiment, structures such as the backlash-less mechanism 237 and the linear guides 251 and 253 can be provided in order to transmit rotation more smoothly, as described in (2-2. Structure of power transmission mechanism) above. Therefore, the configuration of the power transmission mechanism 330 may become complicated and the cost may also end up increasing.

Which of the power transmission mechanism 330 according to the first embodiment and the power transmission mechanism 360 according to the second embodiment to adopt may be suitably determined comprehensively taking into consideration various conditions such as the manufacturing cost of the observation device, operability of the support units 120 and 420, and ease of ensuring clean areas during surgery.

5. Usage Example

Figure 12:
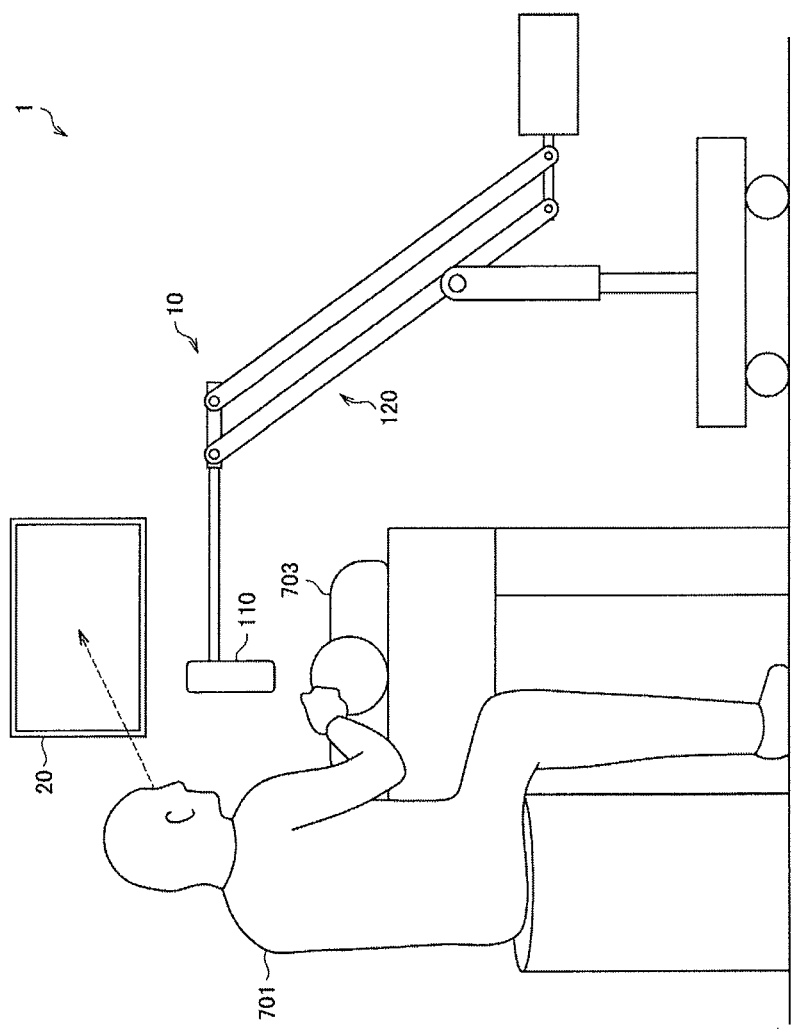
FIG. 12 is a view schematically illustrating a surgical situation in which the observation systems according to the first and second embodiments are used.

An overview of surgery performed using the observation systems 1 and 2 will be described as a usage example of the observation systems 1 and 2 according to the first and second embodiments with reference to FIG. 12. FIG. 12 is a view schematically illustrating a surgical situation in which the observation systems 1 and 2 according to the first and second embodiments are used. In FIG. 12, a surgical situation in which the observation system 1 according to the first embodiment is used is illustrated as an example, but a surgical situation in which the observation system 2 according to the second embodiment is used is similar, aside from the structure of the observation device 10 being modified.

Referring to FIG. 12, a situation in which the surgeon 701 is operating on the head of a patient 703 lying on an operating table is illustrated. The observation device 10 is arranged next to the operating table, and the position and attitude of the microscope unit 110 are controlled by controlling the driving of the actuators provided for the joint units of the support unit 120 so as to capture an image of the surgical site of the head of the patient 703 with the microscope unit 110 that is attached to the distal end of the support unit 120. Note that although illustrated in a simplified manner in FIG. 12, the observation device 10 illustrated in FIG. 12 has a structure similar to the structure of the observation device 10 described with reference to FIG. 4.

The display device 20 is provided in the operating room, and an image of the surgical site captured by the microscope unit 110 of the observation device 10 is magnified at a predetermined magnification and displayed on the display device 20. The surgeon 701 ascertains the state of the surgical site and performs various procedures on the surgical site at hand, while looking at the image displayed on the display device 20.

At this time, the microscope unit 110 of the observation device 10 can be positioned near the surgical site, i.e., near the hands of the surgeon 701, as illustrated in the drawing. Also, the distal end region of the support unit 120 of the observation device 10 can be positioned between the surgeon 701 and the display device 20.

However, as described in (2. First embodiment) above, in the first embodiment, the second joint unit 220 and the actuator 322 that applies driving force with respect to rotation about the second axis $O_2$ that is the rotational axis of the support unit 120 are arranged in positions separated from each other via the power transmission mechanism 330 in the support unit 120. Accordingly, the structure of the distal end region of the support unit 120 is smaller. Thus, the workspace and field of view of the surgeon 701 can be better ensured, so surgery can be performed smoothly. In the illustrated example, the observation device 10 according to the first embodiment is illustrated, but even in a case where the observation device 30 according to the second embodiment is used, the structure of the distal end region of the support unit 420 can similarly be made smaller, so the workspace and field of visibility of the surgeon 701 can be better ensured, thereby enabling surgery to be performed smoothly, as described in (3. Second embodiment) above.

6. Supplemental Remarks

The preferred embodiments of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

For example, in the first and second embodiments described above, the microscope unit 110 is provided on the distal end of the support units 120 and 420, but the present technology is not limited to this example. For example, the microscope unit 110 may be held in a position midway along the support units 120 and 420. Even in this case, by providing a configuration in which, for at least one joint unit capable of defining the attitude of the microscope unit 110, the joint unit and the actuator are separated via the power transmission mechanisms 330 and 360, the structure near the microscope unit 110 is able to be made smaller, so a similar effect as the effect of the first and second embodiments can be obtained.

Also, in the first and second embodiments described above, actuators are provided for all of the joint units 210 to 260 that form the support unit 120, but the present technology is not limited to this example. For example, only one of the joint units 210 to 260 that form the support units 120 and 420 may be provided with an actuator that applies driving force with respect to rotation of the joint unit. In a case where an actuator is provided for at least one joint unit, among joint units capable of defining the attitude of the microscope unit, the present technology can be applied to the at least one joint unit and the actuator. Accordingly, in the configuration of the support unit to which the present technology can be applied, the arrangement of the actuators with respect to the joint units other than the joint unit capable of defining the attitude of the microscope unit may be arbitrary.

Additionally, the present technology may also be configured as below.

(1)

A medical observation device including:

an imaging unit configured to capture an image of an object to be observed, and output a video signal; and a support unit configured with a plurality of arm units rotatably connected to each other via joint units, and configured to support the imaging unit, in which an actuator that applies driving force with respect to rotation about a rotational axis of at least one joint unit that defines an attitude of the imaging unit, among a plurality of the joint units that form the support unit, is provided, and the at least one joint unit and the actuator are arranged separated from each other, and are connected to each other via a power transmission mechanism that transmits rotary movement between two rotational axes that are substantially orthogonal to each other.

(2)

The medical observation device according to (1), in which the at least one joint unit is arranged on one side of one predetermined arm unit, among the arm units that form the support unit, in a manner such that a rotational axis is substantially orthogonal to a direction in which the predetermined arm unit extends, the actuator is arranged on the other side of the predetermined arm unit, in a manner such that a rotational axis is substantially parallel to the direction in which the predetermined arm unit extends, and the power transmission mechanism is provided inside the predetermined arm unit.

(3)

The medical observation device according to (2), in which the actuator is configured with a motor, a reduction mechanism, a clutch, and a brake arranged in series in this order.

(4)

The medical observation device according to (3), in which the actuator is configured such that the size of the motor and the reduction mechanism in an in-plane direction perpendicular to the direction in which the predetermined arm unit extends is smaller than the size of the clutch or the brake in the in-plane direction perpendicular to the direction in which the predetermined arm unit extends.

(5)

The medical observation device according to (3) or (4), in which a potentiometer configured to detect a rotation angle of the least one joint unit is provided in the at least one joint unit, and driving of the at least one joint unit is controlled such that a display of an image of the object to be observed captured by the imaging unit moves in a left-and-right direction or an up-and-down direction, on the basis of a detection value from the potentiometer.

(6)

The medical observation device according to any one of (1) to (5), in which the power transmission mechanism includes
a drive shaft that is connected at one end to a rotating shaft of the actuator and extends in a direction substantially parallel to the rotating shaft of the actuator,
a first bevel gear that is provided on the other end of the drive shaft and rotates on the same axis as the rotating shaft of the actuator, and
a second bevel gear that meshes with the first bevel gear and rotates on the same axis as the rotational axis of the at least one joint unit.

(7)

The medical observation device according to (6), in which the power transmission mechanism further includes a spring that urges the first bevel gear in a direction that reduces a clearance between the first bevel gear and the second bevel gear.

(8)

The medical observation device according to (6) or (7), in which the power transmission mechanism further includes a linear guide that guides movement in an axial direction of the drive shaft.

(9)

The observation device according to any one of (6) to (8), in which the power transmission mechanism further includes a thrust bearing provided on the drive shaft.

(10)

The medical observation device according to any one of (6) to (9), in which the power transmission mechanism further includes an Oldham coupling that connects the rotating shaft of the actuator to the drive shaft.

(11)

The medical observation device according to any one of (1) to (10), in which the imaging unit is provided on a distal end of the support unit, and the at least one joint unit is a joint unit provided second from a distal end side where the imaging unit is provided, in the support unit.

(12)

The medical observation device according to any one of (1) to (5), in which the power transmission mechanism includes
a worm gear formed by
a worm that is connected at one end to a rotating shaft of the actuator and rotates on the same axis as the rotating shaft of the actuator, and
a worm wheel that meshes with a tooth face of the worm and rotates on the same axis as the rotational axis of the at least one joint unit.

(13)

A surgical observation device including:

a microscope unit configured to capture an image of an object to be observed, and output a video signal; and a support unit configured with a plurality of arm units rotatably connected to each other via joint units, and configured to support the microscope unit, in which an actuator that applies driving force with respect to rotation about a rotational axis of at least one joint unit that defines an attitude of the microscope unit, among a plurality of the joint units that form the support unit, is provided, and the at least one joint unit and the actuator are arranged separated from each other, and are connected to each other via a power transmission mechanism that transmits rotary movement between two rotational axes that are substantially orthogonal to each other.

(14)

A medical observation system including:

an observation device configured to include an imaging unit that captures an image of an object to be observed and outputs a video signal, and a support unit which is configured with a plurality of arm units rotatably connected to each other via joint units, and which supports the imaging unit; and a display device configured to display an image of the object to be observed captured by the imaging unit, on the basis of the video signal, in which, in the observation device, an actuator that applies driving force with respect to rotation about a rotational axis of at least one joint unit that defines an attitude of the imaging unit, among a plurality of the joint units that form the support unit, is provided, and the at least one joint unit and the actuator are arranged separated from each other, and are connected to each other via a power transmission mechanism that transmits rotary movement between two rotational axes that are substantially orthogonal to each other.

REFERENCE SIGNS LIST 1, 2 observation system
10, 30 observation device
20 display device
110 microscope unit
120, 140 support unit
130 base unit
140 control device
210 first joint unit
220 second joint unit
230 third joint unit
240 fourth joint unit
250 fifth joint unit
260 sixth joint unit
271 first arm unit
272 second arm unit
273 third arm unit
274 fourth arm unit
275 fifth arm unit
330, 360 power transmission mechanism
231 second bevel gear
233 first bevel gear
235 drive shaft
237 backlash-less mechanism
239 thrust bearing
251, 253 linear guide
255 Oldham coupling
321, 322, 322a, 323, 323a, 324, 325, 326, 327 actuator
341, 351 motor
342, 352 reduction mechanism
343, 353 clutch
344, 354 brake
345, 355 drive shaft
346 potentiometer
361 belt

The invention claimed is:

1. A medical observation device comprising:
a camera configured to capture an image of an object to be observed, and output a video signal;
a support configured with a plurality of arms rotatably connected to each other via joints, and configured to support the camera;
an actuator arranged within a predetermined arm in the plurality of arms that is connected to another arm in the plurality of arms by at least one joint in the plurality of joints that form the support; and
the actuator applies a driving force to a gear in the at least one joint to rotate the another arm around a rotational axis of the at least one joint that defines a position or orientation of the camera, the actuator including a motor, a reduction mechanism, a clutch, and a brake arranged in series in this order, wherein
the at least one joint and the actuator are arranged separated from each other, and are connected to each other via a power transmission mechanism that transmits rotary movement between two rotational axes that are in different directions from each other.

2. The medical observation device according to claim 1, wherein the at least one joint is arranged on one side of one predetermined arm, among the arms that form the support, in a manner such that a rotational axis is substantially orthogonal to a direction in which the predetermined arm extends,
the actuator is arranged on an other side of the predetermined arm, in a manner such that a rotational axis is substantially parallel to the direction in which the predetermined arm extends, and the power transmission mechanism is provided inside the predetermined arm.

3. The medical observation device according to claim 2, wherein the actuator is configured such that a size of the motor and the reduction mechanism in an in-plane direction perpendicular to the direction in which the predetermined arm extends is smaller than a size of the clutch or the brake in the in-plane direction perpendicular to the direction in which the predetermined arm extends.

4. The medical observation device according to claim 2, wherein a potentiometer configured to detect a rotation angle of the least one joint is provided in the at least one joint, and
driving of the at least one joint is controlled such that a display of an image of the object to be observed captured by the camera moves in a left-and-right direction or an up- and-down direction, on a basis of a detection value from the potentiometer.

5. The medical observation device according to claim 1, wherein the power transmission mechanism includes
a drive shaft that is connected at one end to a rotating shaft of the actuator and extends in a direction substantially parallel to the rotating shaft of the actuator,
a first bevel gear that is included in the gear and that is provided on an other end of the drive shaft and rotates on a same axis as the rotating shaft of the actuator, and a second bevel gear that meshes with the first bevel gear and rotates on a same axis as the rotational axis of the at least one joint.

6. The medical observation device according to claim 5, wherein the power transmission mechanism further includes a spring that urges the first bevel gear in a direction that reduces a clearance between the first bevel gear and the second bevel gear.

7. The medical observation device according to claim 6, wherein the power transmission mechanism further includes a linear guide that guides movement in an axial direction of the drive shaft.

8. The medical observation device according to claim 6, wherein the power transmission mechanism further includes a thrust bearing provided on the drive shaft.

9. The medical observation device according to claim 5, wherein the power transmission mechanism further includes an Oldham coupling that connects the rotating shaft of the actuator to the drive shaft.

10. The medical observation device according to claim 1, wherein the camera is provided on a distal end of the support, and
the at least one joint is a joint provided second from a distal end side where the camera is provided, in the support.

11. The medical observation device according to claim 1, wherein the power transmission mechanism includes
a worm gear formed by
a worm that is included in the gear and that is connected at one end to a rotating shaft of the actuator and rotates on a same axis as the rotating shaft of the actuator, and
a worm wheel that meshes with a tooth face of the worm and rotates on a same axis as the rotational axis of the at least one joint.

12. A surgical observation device comprising:
a microscope configured to capture an image of an object to be observed, and output a video signal;
a support configured with a plurality of arms rotatably connected to each other via joints, and configured to support the microscope;
an actuator arranged within a predetermined arm in the plurality of arms that is connected to another arm in the plurality of arms by at least one joint in the plurality of joints that form the support; and
the actuator applies a driving force to a gear in the at least one joint to rotate the another arm around a rotational axis of at least one joint that defines a position or orientation of the microscope, the actuator including a motor, a reduction mechanism, a clutch, and a brake arranged in series in this order, wherein
the at least one joint and the actuator are arranged separated from each other, and are connected to each other via a power transmission mechanism that transmits rotary movement between two rotational axes that are in different directions from each other.

13. A medical observation system comprising:
an observation device that includes a camera that captures an image of an object to be observed and outputs a video signal, and a support configured with a plurality of arms rotatably connected to each other via joints, and configured to support the camera; and
a display device configured to display an image of the object to be observed captured by the camera, on a basis of the video signal, wherein, in the observation device,
an actuator is arranged within a predetermined arm in the plurality of arms that is connected to another arm in the plurality of arms by at least one joint in the plurality of joints that form the support,
the actuator applies a driving force to a gear in the at least one joint to rotate the another arm around a rotational axis of the at least one joint that defines a position or orientation of the camera, the actuator including a motor, a reduction mechanism, a clutch, and a brake arranged in series in this order, and
the at least one joint and the actuator are arranged separated from each other, and are connected to each other via a power transmission mechanism that transmits rotary movement between two rotational axes that are in different directions from each other.

14. The medical observation device according to claim 1, wherein the two rotational axes that are in different directions from each other are substantially orthogonal to each other.

15. A medical device comprising:
a support configured with a plurality of arms rotatably connected to each other via joints and configured to support a camera; and
an actuator arranged within a predetermined arm in the plurality of arms that is connected to another arm in the plurality of arms by at least one joint in the plurality of joints that form the support, wherein
the actuator applies a driving force to a gear in the at least one joint to rotate the another arm around a rotational axis of the at least one joint that defines a position or orientation of the camera,
the at least one joint and the actuator are arranged separated from each other, and are connected to each other via a power transmission mechanism that transmits rotary movement between two rotational axes that are in different directions from each other, the power transmission mechanism including a drive shaft arranged between the at least one joint and the actuator, and a length of the drive shaft being greater than half of the length of the predetermined arm, and
the actuator is arranged in a proximal end portion of the predetermined arm, the proximal end portion being at an end of the predetermined arm that is furthest from the camera along a longest dimension of the predetermined arm.

16. The medical device according to claim 15, wherein:
the camera includes a microscope configured to capture a magnified image of an object to be observed and output a video signal.

17. The medical device according to claim 15, wherein the at least one joint is arranged on one side of one predetermined arm, among the arms that form the support, in a manner such that a rotational axis is substantially orthogonal to a direction in which the predetermined arm extends,
the actuator is arranged on an other side of the predetermined arm, in a manner such that a rotational axis is substantially parallel to the direction in which the predetermined arm extends, and
the power transmission mechanism is provided inside the predetermined arm.

18. The medical device according to claim 17, wherein the actuator is configured such that a size of a motor and a reduction mechanism in an in-plane direction perpendicular to the direction in which the predetermined arm extends is smaller than a size of a clutch or a brake in the in-plane direction perpendicular to the direction in which the predetermined arm extends.

19. The medical device according to claim 15, wherein the power transmission mechanism includes
the drive shaft that is connected at one end to a rotating shaft of the actuator and extends in a direction substantially parallel to the rotating shaft of the actuator,
a first bevel gear that is included in the gear and that is provided on an other end of the drive shaft and rotates on a same axis as the rotating shaft of the actuator, and
a second bevel gear that meshes with the first bevel gear and rotates on a same axis as the rotational axis of the at least one joint.

20. The medical device according to claim 15, wherein the two rotational axes that are in different directions from each other are substantially orthogonal to each other.

21. The medical device according to claim 15, wherein the actuator rotates in a first rotational direction and applies the driving force to the gear in the at least one joint to rotate the another arm in a second rotational direction that is different from the first rotational direction.

22. The medical device according to claim 21, wherein the first rotational direction is one of a clock-wise direction and a counter-clock-wise direction, and the second rotational direction is the other one of the clock-wise direction and the counter-clock-wise direction.

* * * * *